United States Patent [19]

Grunwell et al.

[11] 4,022,769

[45] May 10, 1977

[54] ANDROST-4-EN-19-ONES

[75] Inventors: Joyce F. Grunwell, Hamilton; Vladimir Petrow, Cincinnati, both of Ohio

[73] Assignee: Richardson-Merrell Inc., Wilton, Conn.

[22] Filed: May 13, 1974

[21] Appl. No.: 469,480

[52] U.S. Cl. .............. 260/239.55 R; 260/239.55 C; 260/397.3; 260/397.4; 260/397.5; 424/241; 424/243

[51] Int. Cl.$^2$ ......................................... C07J 1/00

[58] Field of Search ................... 260/397.4, 239.55

[56] References Cited

UNITED STATES PATENTS

| | | | |
|---|---|---|---|
| 3,142,689 | 7/1964 | Kersten et al. | 260/397.3 |
| 3,170,934 | 2/1965 | Wettstein et al. | 260/397.1 |
| 3,284,448 | 11/1966 | Cross | 260/239.55 |
| 3,417,111 | 12/1968 | Knox | 260/397.1 |
| 3,431,287 | 3/1969 | DeWinter | 260/397.4 |
| 3,449,381 | 6/1969 | Bowers | 260/397.4 |
| 3,458,539 | 7/1969 | Wettstein et al. | 260/397.1 |
| 3,506,549 | 4/1970 | Throop et al. | 204/75 |

FOREIGN PATENTS OR APPLICATIONS

| | | | |
|---|---|---|---|
| 1,370,970 | 9/1963 | France | 260/397.3 |

OTHER PUBLICATIONS

Rao et al., Journ. Org. Chem., vol. 27, No. 12, pp. 4694-4695, (1962).

Applezweig, Steroid Drugs, vol. 1, pp. 312, 316 & 317, McGraw-Hill Book Co., 1962.

*Primary Examiner*—Ethel G. Love
*Attorney, Agent, or Firm*—William J. Stein; Eugene O. Retter; George W. Rauchfuss, Jr.

[57] ABSTRACT

The present invention concerns derivatives of androst-4-en-19-one which are useful in the enhancement of libido and related psychic attitudes.

2 Claims, No Drawings

ANDROST-4-EN-19-ONES

SUMMARY OF THE INVENTION

This invention relates to new derivatives of androst-4-en-19-one, to their preparation and use as pharmaceutical agents. More particularly, the novel compounds of this invention are represented by the formula:

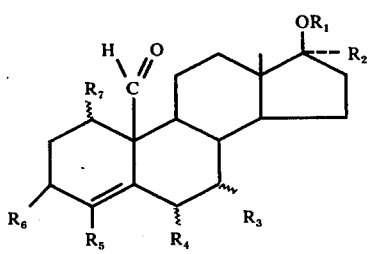

wherein $R_1$ and $R_8$ are each selected from the group consisting of hydrogen, acyl having from 1 to 12 carbon atoms, lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxy-cycloalkyl in which the cycloalkyl group has from 5 to 7 carbon atoms;

$R_2$ is selected from the group consisting of hydrogen, lower alkyl having from 1 to 6 carbon atoms, lower alkynyl having from 2 to 6 carbon atoms, lower alkynyl having from 2 to 6 carbon atoms, and when $R_2$ and $OR_1$ are taken together is oxo;

$R_3$, $R_4$, $R_5$ and $R_7$ are hydrogen and methyl; and $R_6$ is selected from the group consisting of $H_2$, oxo, and $H(OR_8)$ with the proviso that when $R_6$ is oxo and $R_3$, $R_4$, $R_5$ and $R_7$ are all hydrogen then $R_1$ cannot by hydrogen, acyl, 2-tetrahydropranyl or oxo when taken together with $R_2$.

This invention also relates to the unexpected and surprising discovery that the novel compounds described in formula (I) above, in addition to certain compounds previously described in the prior art, possess the property of enhancing a dimished libido in mammals without evoking any overt androgenic or estrogenic response upon the secondary sex structures. More particularly, the class of compounds which possess this novel utility is represented by the formula:

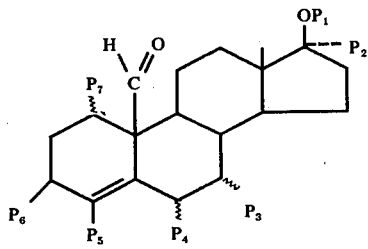

wherein $P_1$ and $P_8$ are each selected from the group consisting of hydrogen, acyl having from 1 to 12 carbon atoms, lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms, $P_2$ is selected from the group consisting of hydrogen, lower alkyl having from 1 to 6 carbon atoms, lower alkenyl having from 2 to 6 carbon atoms, lower alkynyl having from 2 to 6 carbon atoms, and when $P_2$ and $OP_1$ are taken together is oxo, $P_3$, $P_4$, $P_5$ and $P_7$ are hydrogen and methyl, and $P_6$ is selected from the group consisting of $H_2$, oxo, and $H(OP_8)$.

DESCRIPTION OF THE PRIOR ART

U.S. Pat. No. 3,077,482 discloses the preparation of $\Delta^4$-3:19-dioxo-17$\beta$-($\beta$-phenylpropionyloxy) androstene and $\Delta^4$-3:19-dioxo-17$\alpha$-ethinyl-17$\beta$-hydroxyandrostene as intermediates in the preparation of the corresponding 19-acids, which in turn are decarboxylated to form the corresponding 19-nor compounds.

U.S. Pat. No. 3,170,934 also discloses the preparation of $\Delta^4$-3:19-dioxo-17$\beta$-($\beta$-phenylpropionyloxy)androstene and $\Delta^4$-3:19-dioxo-17$\alpha$-ethinyl-17$\beta$-hydroxyandrostene as intermediates in the preparation of the corresponding 19-acids and 19-nor compounds.

Rao and Axelrod, J. Org. Chem, 27, 4694–6 (1962), describe the preparation of 3,17,19-trioxo-4-androstene, 3,19-dioxo-4-androsten-17$\beta$-ol and 3,19-dioxo-4-androsten-17$\beta$-(2'-tetrahydropyranyl)ether. No use is given for these compounds, however, other than existence and confirmation as metabolites of testosterone 4-$C^{14}$ when incubated with certain human polycystic ovarian tissues.

U.S. Pat. No. 3,449,381 discloses certain 19-oxo and 19-loweralkyl-19-oxo-androstane derivatives. More particularly, the compounds which are most closely related to the novel compounds of the present invention include the compound 17$\beta$-hydroxy-androst-4-en-3,19-dione, its 17$\beta$-acylates and the 17$\alpha$-lower alkyl, alkenyl and alkinyl derivatives thereof. These compounds are stated to exhibit anabolic-androgenic activity, inhibit the production of pituitary gonadotropic hormones and A.C.T.H., possess anti-estrogenic properties, lower blood, liver and adrenal chlorosterol levels, to be useful in the control of fertility and psychotic conditions and as appetite stimulants.

Hormones are generally recognized as being of significance in the biochemical regulation of the psyche and sexual behavior, Hubble, Lancet, Aug. 3, 1963, 209–214. However, none of the references above teach or suggest the unexpected properties which the novel compounds of this invention possess, namely, the unexpected and remarkable ability of these compounds to enhance the sexual interest and drive of mammels. Furthermore, these compounds can be used without obtaining any overt, concomitant, androgenic, somatic side effects.

DETAILED DESCRIPTION OF THE INVENTION

As shown in formula (I) above, the novel compounds of the present invention are substituted in the 1,3,4,6,7 and 17-positions of the androst-4-en-19-one nucleus.

The symbol $OR_1$ represents various oxygenated substituents located at the 17$\beta$-position of this nucleus. Suitable substituents include the hydroxyl group, an acyl ester and various lower alkyl, silyl, tetrahydropyranyl, saturated and unsaturated ethers. When $R_1$ represents hydrogen, the 17$\beta$-hydroxyl group is present.

When $R_1$ represents acyl, an acyl ester derived from a monobasic alkyl, aryl or aralkyl carboxylic acid having from 1 to 12 carbon atoms is present at the 17β-position. The carboxylic acids from which these acylates are derived include saturated and unsaturated aliphatic acids as well as aromatic acids, as for example, acetic, propionic, butyric, isobutyric, valeric, isovaleric, caproic, caprylic, decanoic, dodecanoic, acrylic, crotonic, cyclobutanecarboxylic, cyclopentanecarboxylic, cyclopentenecarboxylic, cyclohexanecarboxylic, benzoic, toluic, naphthoic, ethylbenzoic, phenylacetic, naphthaleneacetic, phenylvaleric, cinnamic, phenylpropionic, p-propyloxyphenylpropionic and p-butyloxyphenylacetic acid.

The term lower alkyl as used with regard to the ether substitution in the 17β-position refers to groups having from 1 to 3 carbon atoms, as for example, methyl, ethyl, propyl and isopropyl. Silyl ethers containing a tetrasubstituted silicon atom are similarly substituted with three lower alkyl groups having from 1 to 5 carbon atoms. Alternatively, the silicon atom can be substituted with three phenyl radicals. Ethers which are present in the 17β-position also include unsaturated cycloalkane ethers having from 5 to 7 carbon atoms in which the unsaturation is present in a position alpha to the ether oxygen as represented by the term 1-cycloalkenyl. Illustrative of such groups are the 1-cyclopentyl, 1-cyclohexenyl or 1-cycloheptenyl radicals. The corresponding saturated cycloalkane ethers are also considered to be within the scope of this invention but here the cycloalkane group is further substituted with a methoxy or an ethoxy radical at its point of attachment, i.e, at the 1-position of the cycloalkyl ring. Typical of the saturated heterocyclic radicals which are present as ethers in the 17β-position are the 2-tetrahydropyranyl and the 4-tetrahydropyranyl radicals.

The symbol $R_2$ represents the 17α-position and can be either a hydrogen atom or a saturated or unsaturated aliphatic chain having from 1 to 6 carbon atoms. Illustrative of such groups are straight or branched chain alkyl radicals, as for example, methyl, ethyl, propyl, isopropyl, butyl, sec-butyl, isoamyl, n-pentyl and n-hexyl. Illustrative of the alkenyl groups which can be present are the vinyl, allyl, 1-butenyl, 1-pentenyl and 1-hexenyl radicals. Illustrative of the alkynyl groups which may be present are the ethynyl, 1-propynyl and 1-butynyl radicals. It should be not that the symbols $R_2$ and $OR_1$ when taken together can also represent an oxo radical, thereby forming a class of substituted androst-4-en-17,19-diones.

The symbols $R_3$, $R_4$, $R_5$ and $R_7$ represent hydrogen or methyl. Thus, any or all of the 1,4,6 and 7-positions of the androst-4-en-19-one nucleus can either remain unsubstituted, as when the various symbols represent hydrogen, or they may be individually substituted with a methyl group.

The symbol $R_6$ represents various substituents located at the 3-position of this nucleus. Suitable substituents include two hydrogen atoms, an oxo group, and either a substituted or an unsubstituted hydroxyl group. The substituted or unsubstituted hydroxyl group, represented by the symbol $OR_8$, can be present in either the alpha or beta configuration. When the symbol $R_8$ represents hydrogen, the free alcohol is, of course, delineated. When the symbol $R_8$ represents acyl, an ester is present at the 3-position. These esters are derived from the same monobasic alkyl, aryl or aralkyl carboxylic acids having from 1 to 12 carbon atoms which are enumerated above for $R_1$ at the 17β-position. Finally, the 3-ethers are dilineated when the symbol $R_8$ represents lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms.

In order to exclude certain prior art compounds from the novel compounds being claimed, a proviso limitation is included for $R_6$ at the 3-position. Thus, whenever an oxo group is present at the 3-position and the 1,4,6 and 7-positions are substituted with hydrogen, then the 17β-position must be an ether other than the 2-tetrahydropyranyl ether. Thus, the 17β-position cannot be substituted with a hydroxy group or its acyl ester, a 2-tetrahydropranyl ether or an oxo group when taken together with the 17α-substitution, i.e., when $R_6$ is oxo and $R_3$, $R_4$, $R_5$ and $R_7$ are all hydrogen, then $R_1$ cannot be hydrogen, acyl, 2-tetrahydropyranyl or oxo when taken together with $R_2$.

Excluded from the scope of the novel compounds described herein are: 17β-hydroxy-androst-4-ene-3,19-dione, androst-4-ene-3,17,19-trione, 17β-(2'-tetrahydropyranyloxy)androst-4-ene-3,19-dione, 17β-hydroxy-androst-4-ene-3,19-dione acetate, 17β-hydroxy-androst-4-ene-3,19-dione benzoate, 17β-hydroxy-17α-(lower alkyl)androst-4-ene-3,19-diones, 17β-hydroxy-17α-(lower alkyl)androst-4-ene-3,19-dione acylates, 17β-hydroxy-17α-(lower alkenyl)androst-4-ene-3,19-diones, 17β-hydroxy-17α-(lower alkenyl)androst-4-ene-3,19-dione acylates, 17β-hydroxy-17α-(lower alkynyl)androst-4-ene-3,19-diones, and 17β-hydroxy-17α-(lower alkynyl)androst-4-ene-3,19-dione acylates.

The symbols $OR_1$ and $OR_8$ at the 17β- and 3α- or 3β-positions represent identical substituents. Each can represent either a free hydroxyl group, its acyl ester or an ether and can be varied independently of one another.

A preferred class of compounds includes the 3β-alcohols of androst-4-en-19-one. These compounds are delineated where the symbol $R_6$ represents $H(OR_8)$ and the symbol $R_8$ is hydrogen. Illustrative species encompassed within this preferred class of compounds include: 3β,17β-dihydroxy-1-methyl-androst-4-en-19-one, 17α-ethyl-3β,17β-dihydroxy-4-methyl-androst-4-en-19-one, 3β-hydroxy-1,7-dimethyl-androst-4-ene-17,19-dione, 3β,17β-dihydroxy-6-methyl-17α-(1'-propenyl)-androst-4-en-19-one 17-acetate, 17α-hexyl-3β-hydroxy-1,4-dimethyl-androst-4-en-19-one, 17α-ethynyl-3β,17β-dihydroxy-7-methyl-androst-4-en-19-one, 3β-hydroxy-1,4,6-trimethyl-androst-4-ene-17,19-dione, 3β-hydroxy-1,7-dimethyl-17β-(4'-tetrahydropyranyloxy)androst-4-en-19-one, 3β,17β-dihydroxy-1,4,6,7-tetramethyl-androst-4-en-19-one 17-decanoate, 17α-butyl-17β-(1'-cycloheptenyloxy)-3β-hydroxy-androst-4-en-19-one, 3β-hydroxy-1,7-dimethy-17α-(1'-propenyl)-17β-triphenylsilyloxy-androst-4-en-19-one, 3β,17β-dihydroxy-7,17β-dimethyl-androst-4-en-19-one, 17β-(1'-ethoxycyclopentyloxy)-3β-hydroxy-6-methyl-androst-4-en-19-one, 17α-ethynyl-3β-hydroxy-1-methyl-17β-trimethylsiloxy-androst-4-en-19-one and 3β-hydroxyl-1,6,7-trimethyl-androst-4-ene-17,19-dione.

Another preferred group of compounds are the 3α or 3β-ethers of androst-4-en-19-one. These compounds are delineated where the symbol $R_6$ repesents $H(OR_8)$ and the symbol $R_8$ is lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms. Illustrative species encompassed within this preferred class of compounds include: 3β-methoxy-1-methyl-androst-4-ene-17,19-dione, 7-methyl-3β-trimethylsiloxy-androst-4-ene-17,19-dione, 1,4-dimethyl-3β-triphenylsiloxy-androst-4-ene-17,19-dione, 17α-ethyl-17β-hydroxy-4-methyl-3β-(2'-tetrahydropyranyloxy)-androst-4-en-19-one, 3β-(1'-cyclopentenyloxy)-17α-ethynyl-17β-hydroxy-6-methyl-androst-4-en-19-one, 3β-(1'-methoxycyclohexyloxy)-17α-propenyl-1,4,7-trimethyl-androst-4-en-19-one, 6-methyl-3β-propoxy-androst-4-ene-17,19-dione, 1-methyl-3β-(4'-tetrahydropyranyloxy)-androst-4-ene-17,19-dione, 17β-hydroxy-7-methyl-3β-triethylsiloxy-androst-4-en-19-one acetate, 3β-(1'-cycloheptenyloxy)-17β-hydroxy-1,7-dimethyl-androst-4-en-19-one decanoate, 17β-hydroxy-3β-methoxy-4-methyl-17α-pentyl-androst-4-en-19-one, 3β-(1'-ethoxycyclopentyloxy)-17α-ethynyl-17β-hydroxy-1,4,6,7-tetramethyl-androst-4-en-19-one, and 17β-hydroxy-3β-triphenylsiloxy-androst-4-en-19-one.

A final group of preferred compounds are the 3β,17β-diethers of androst-4-en-19-one. The ether substituents at positions 3 or 17 encompassed within this class of compounds can be either the same or different. This class of compounds is delineated where $R_6$ is $H(OR_8)$ and both $R_1$ and $R_8$ are lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms. Illustrative compounds encompassed within this group are 3β-methoxy-4-methyl-17β-(4'-tetrahydropyranyloxy)-androst-4-en-19-one, 1,6-dimethyl-3β,17β-dipropoxy-17α-methyl-androst-4-en-19-one, 7-methyl-17β-propoxy-3β-(trimethylsiloxy)-androst-4-en-19-one, 4-methyl-3β-(2'-tetrahydropyranyloxy)-17β-triphenylsiloxy-17α-vinyl-androst-4-en-19-one, 3β,17β-di-(1'-cyclopentenyloxy)-17α-ethynyl-androst-4-en-19-one, 3α-methoxy-17β-(1'-methoxycyclohexyloxy)-6,17α-dimethyl-androst-4-en-19-one, 17β-ethoxy-3β-triphenylsiloxy-androst-4-en-19-one, 3β,17β-di-(2'-tetrahydropyranyloxy)-17α-(1'-propenyl)-androst-4-en-19-one, 3β-(1'-methoxycycloheptanyloxy)-1,4-dimethyl-17β-propoxy-androst-4-en-19-one, 17α-ethynyl-3β,17β-di-(trimethylsiloxy)-androst-4-en-19-one, 4-methyl-3β-propoxy-17β-(2'-tetrahydropyranyloxy)-androst-4-en-19-one, 17α-butyl-3β,17β-di(1'-ethoxycyclohexyloxy)-androst-4-en-19-one, 3β-(1'-cyclohexenyloxy)-17α-ethenyl-1,4,6,7-tetramethyl-17β-triphenylsiloxy-androst-4-en-19-one, and 3β-ethoxy-17β-(1'-methoxycyclopentyloxy)-17α-pentyl-androst-4-en-19-one.

The novel alkyl ethers are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as silver oxide or barium oxide in polar, aprotic solvents as for example, dimethylformamide, dimethyl sulfoxide and hexamethylphosphoramide. Using conventional techniques the hydroxyl groups can also be silylated by reaction with silylating agents such as trialkylchlorosilane, triarylchlorosilane, N-trialkylsilylacetamide in the presence of an amine base such as triethylamine or pyridine to prepare the novel silyl ethers.

The 2-tetrahydropyranylethers are prepared from the corresponding hydroxysteroids by reaction with dihydropyran in the presence of an acid catalyst, as for example, hydrochloric acid, p-toluenesulfonic acid or phosphorous oxychloride. The 4-tetrahydropyranyl ethers are prepared by reacting the hydroxysteroid, 4-bromotetrahydropyran and a base such as sodium hydride together in a polar, aprotic solvent as for example, dimethylformamide, dimethylsulfoxide or hexanemethylphosphoramide.

The 1-alkoxycycloalkoxy derivatives are prepared by reacting the hydroxysteroids with a loweralkylketal of a cycloalkanone or the lower alkylenol ether of a cycloalkanone or mixture of these reagents in the presence of an acidic catalyst such as p-toluenesulfonic acid, pyridine hydrochloride, pyridine p-toluenesulfonate. The reaction is generally conducted in a solvent such as dioxane, methylene chloride, ether, t-butanol at a temperature less than 70° C., and preferably at 25° C. The preparation of suitable cycloalkyl derivatives is achieved using such reagents as cyclopentanone diethylketal, cyclohexanone dimethylketal, 1-methoxy-1-cyclopentene or 1-ethoxy-1-cyclohexene. Following essentially the same procedure, the 1-cycloalkenyl ethers are prepared directly using, however, higher boiling solvents so that the reaction temperature is above 70° C. Suitable solvents include benzene, toluene and dimethylformamide. Alternatively, the 1-cycloalkenylethers can be prepared via pyrolysis of the isolated 1-alkoxycycloalkoxysteroid in the presence of a trace of an organic base such as pyridine utilizing a high boiling solvent such as benzene or dimethylformamide. Acyl groups are introduced by standard methods such as the reaction of an alcohol with an acid anhydride or chloride in the presence of an alkaline component such as pyridine.

The 1,4 and 6-methylated derivatives for the 4-androstene-3,19-diones of the present invention are best prepared by introducing the desired methyl group into the 19-hydroxy-androstene and oxidizing the 19-alcohol to the aldehyde. The 1α-methyl-19-hydroxy-4-androsten-3-ones which can be oxidized to the aldehydes are prepared in two steps. The reaction of dichlorodicyanobenzoquinone with a 19-hydroxy-4-androsten-3-one in refluxing dioxane or methylene chloride for 24–72 hours to produce the corresponding 19-hydroxy-1,4-androstadien-3-one. However, two restrictions in this sequence are necessary. First, the 19-hydroxy group must be protected as an ester or an ether in order to avoid aromatization. Secondly, the 1-position must possess an axial hydrogen atom suitable for elimination. Thus, the 1α-methyl androstene is not reactive although the 1β-methyl androstane is. Following this procedure 17β,19-dihydroxy-7α-methyl-4-androsten-3-one dipropionate is converted to 17β,19-dihydroxy-7α-methyl-1,4-androstadien-3-one dipropionate. Similarly, 19-hydroxy-6α-methyl-4-androstene-3,17-dione acetate forms 19-hydroxy-6α-methyl-1,4-androstadiene-3,17-dione acetate and 1β- methyl-19-tetrahydropyranyloxy-4-androstene-3,17-dione forms 1-methyl-19-tetrahydropyranyloxy-1,4-androstadiene-3,17-dione.

The 1α-methyl-19-substituted-androst-4-enes are produced by reacting the corresponding androsta-1,4-dien-3-ones with dimethyllithium copper. Methylation is preferably conducted by adding the androsta-1,4-dien-3-one dissolved in an inert solvent, to a solution of dimethyllithium copper in the same or a different inert solvent. Suitable inert reaction solvents include methylene chloride, tetrahydrofuran, dioxane, hexane, benzene with diethyl ether being the solvent preferred. The reaction is conducted at temperatures between −75° C. and 20° C. with a temperature range from about −5° C. to 0° C. being preferred. The ratio of reactants is not critical, but at least 2 molar equivalents of dimethyllithium copper must be present for each conjugate addition. The presence of free hydroxyl groups will, of course, require additional equivalent amounts of the organometallic reagent. Following this procedure, 19-hydroxy-androst-1,4-diene-3,17-dione propionate can be converted to 19-hydroxy-1α-methyl-androst-4-en-3,17-dione propionate.

The 1β-methyl-19-substituted-4-androsten-3-ones are synthesized in the manner of Simmons and Smith by treatment of a 19-substituted-androsta-1,5-diene-3β-ol with methylenediiodide and a zinc-copper couple to form the 19-substituted-1β,2β-methylene-androst-5-en-3β-ol. The presence of the 3β-alcohol as well as the 19-alcohol direct the insertion to the beta side. The 1β,2β-methylene-3β-ol is then oxidized to a 3-one and the cyclopropyl ring cleaved by acid or base to form the 19-substituted-1β-methyl-4-androsten-3-one. Typically a mixture of zinc-copper couple, iodine and methylenediiodide in an inert solvent such as diethylether, tetrahydrofuran, dioxane or diglyme is heated with an infrared lamp for 30 minutes. The steroid, also in an inert solvent as above, is added and the mixture heated from 25° to 100° for 30 minutes to 72 hours. Generally, reflux temperatures of the solvent employed combined with a 24 hour reflux period is sufficient. The Simmons-Smith reagent is taken in 5–10 fold excess. The oxidation of the 3-alcohol is readily achieved with various oxidizing agents. Illustrative oxidizing agents are Jones reagent, $CrO_3$ pyridine complex (Sarett reagent), and Cornforth reagent. However, the 19-alcohol must be protected to avoid being over-oxidized. The remaining 1β,2β-methylene ring is then cleaved to the 1β-methyl group by refluxing with zinc in acetic acid. In this manner 19-tetrahydropyranyloxy-1,5-androstadiene-3,17-diol is converted to 1β-methyl-19-hydroxy-4-androstene-3,17-dione.

Methylation of 19-hydroxy-4-androsten-3-ones using Atwater's procedure (N. W. Atwater, J. Am. Chem. Soc. 79, 5315 (1957)) of adding methychloride slowly to a refluxing solution of the ketone in t-butanol containing only a small excess of potassium t-butoxide produces the 19-hydroxy-4-methyl-4-androsten-4-androsten-3-ones in fair yield. Following this procedure 19-hydroxy-7α-methyl-androst-4-ene-3,17-dione and 17β,19-hydroxy-1α,7α-dimethyl-androst-4-en-3-one can be converted to 19-hydroxy-4,7α-dimethyl-androst-4-ene-3,17-dione and 17β,19-dihydroxy-1α,4-,7α-trimethyl-androst-4-en-3-one, respectively.

Alternatively, the 19-hydroxy-4-androsten-3-one can be selectively thiomethylated at position 4 with formaldehyde and a thiol under basic conditions. Benzylmercaptan is the preferred thiol. Desulphurisation of the intermediate 19-hydroxy-4-phenylthiomethyl-4-androsten-3-one leads to the monomethylated 19-hydroxy-4-methyl-4-androsten-3-one in good yield.

Treatment of a 5α,6α-epoxyandrostane-3,19-diol or a 3,3-ethylenedioxy-5α,6α-epoxyandrostan-19-ol with methylmagnesium bromide in dry solvents such as diethyl ether, tetrahydrofuran, benzene or toluene at temperatures between 0° C. to 100° C., results in epoxide cleavage to give the corresponding 6β-methyl-androstane-5α,19-diols. The corresponding 3-alcohol can be oxidized or the ketal group hydrolyzed with hot acetic acid or dilute aqueous methanolic mineral acid to form the 5α-hydroxy-6β-methyl-3-ketone. Dehydration of the β-hydroxy ketone with sodium hydroxide in hot aqueous methanol is accompanied by inversion at 6 to form 6α-methylandrost-4-en-3-one. In this manner the compounds 17β,19-dihydroxy-6α-methyl-4-androsten-3-one, 17β-hydroxy-6α,17α-dimethyl-4-androstene-3,19-dione are prepared starting with 3,3-ethylenedioxy-5α,6α-epoxyandrostan-17,19-diol and 5α,6α-epoxy-17α-methylandrostan-3β,17β,19-diol, respectively.

The 19-alcohol can be oxidized to the 19-aldehyde by two procedures that avoid over-oxidation to the 19-acid. A Jones oxidation utilizing exactly one equivalent of Jones reagent and conducted in the cold, preferably between −20° C. and 10° C., yields the aldehyde. Also the Pfitzner-Moffatt procedure utilizing dimethylsulfoxide, dicyclohexylcarbodiimide, pyridine and trifluoroacetic acid in benzene at room temperature also produces the 19-aldehyde from the 19-alcohol.

The 19-hydroxy-androst-4-en-3-ones used in the present invention are, broadly speaking, prepared by the methods described in Vol. 11 of Organic Reactions in Steroid Chemistry, Edited by J. Fried and J. A. Edwards, p. 237–87; van Nostrand Reinhold Company, N.Y., (1972). One route to the 19-hydroxyandrost-4-en-3-ones proceeds from the 5α-halogen-6β,19-ether intermediates. These compounds are prepared from the corresponding 5,6-unsaturated steroids by the addition of a hypohalous acid forming the 5α-halogen-6β-carbinols, which are subsequently cyclized by means of lead tetraacetate or by decomposition of the 6β-hypohalites to yield the desired 5α-halogen-6β,19-ethers. Thus, for example, 3β,17β-dihydroxy-5-androstene diacetate is converted to 5α-bromo-3β, 6β,17β-trihydroxyandrostane 3,17-diacetate by means of hypobromous acid. Lead tetraacetate or hypoiodite converts this to 5α-bromo-3β,17β-dihydroxy-6β,19-oxidoandrostane 3,17-diacetate. Likewise, 3β-hydroxyandrost-5-en-17-one acetate is converted to 5α-chloro-3β,6β-dihydroxyandrostan-17-one 3-acetate by means of hypochlorous acid. A lead tetraacetate or hypoiodite oxidation converts this latter compound into 5α-chloro-3β-hydroxy-6β,19-oxidoandrostane-17-one acetate. This 17-acetone reacts with ann organometallic reagent such as methylmagnesium bromide or lithium acetylide to form the desired 17α-alkylated 17β-hydroxy derivative.

The 3-oxo-4-ene group is next introduced by oxidizing the 3β-hydroxy-5α-halo-6β,19-oxido intermediate with an oxidizing agent such as chromium trioxide. Subsequent dehydrohalogenation using pyridine or sodium acetate in methanol results in the formation of the corresponding 6β,19-oxidoandrost-4-en-3-one. This 6β,19-ether is reductively cleaved using reagents such as zinc and isopropanol, zinc and acetic acid or lithium and ammonia to form the desired 19-hydroxyandrost-4-en-3-one. In addition to providing the 19-hydroxyandrostane starting materials for either introduction of methyl groups at 1,4,6,7 either singly or in combinations, this reaction sequence can be conducted with the methyl groups already present in order to prepare the desired intermediates.

An alternative route to the 19-hydroxyandrost-4-en 3-ones proceeds from the 6β,19-oxido-3α,5α-cycloandrostanes as intermediates. These compounds are in turn prepared by a lead tetraacetate or hypoiodite oxidation upon the corresponding 6β-hydroxy-3α,5α-cycloandrostane, an i-steroid. Heating the 6β,19-ether in a solvent such as dimethylsulfoxide with benzoylperoxide results in cleavage and the direct formation of the 19-hydroxyandrost-4-en-3-one. Alternatively, the 6β,19-ether can be cleaved to the corresponding 3β,19-dihydroxy-5-androstene using sulfuric acid in an aqueous acetone solution. This compound is then oxidized to the desired 19-hydroxyandrost-4-en-3-one by means of an Oppenauer oxidation.

The 7α-methyl-4-androstene-3,19-diones are produced by alkylating the corresponding 4,6-androstadiene-3,19-dione with dimethyllithium copper in an inert solvent such as diethyl ether, tetrahydrofuran, hexane or mixtures of these at temperatures ranging from −78° C. to 25° C. Tetrahydrofuran is the preferred solvent and temperatures between −5° C. to 10° C. to provide optimum results. Quenching the initially formed enolate anion with a weak protonating agent such as a saturated solution of ammonium chloride, oxalic acid or boric acid provides the 7α-methyl-5-androstene-3,19-diones. Quenching the enolate with a strong protonating agent such as hydrochloric acid provides the 7α-methyl-4-androstene-3,19-diones.

The 7α-methyl-4-androstene-3,19-dione can also be prepared by either acid or base catalyzed isomerization of the corresponding 7α-methyl-5-androstene-3,19-dione. Suitable acid catalysts include hydrochloric acid, sulfuric acid, p-toluenesulfonic acid and acetic acid and they can be used in such solvents as methanol, ethanol, dioxane, tetrahydrofuran and methylenechloride. Suitable base catalysts for this isomerization includes sodium hydroxide or sodium methoxide in an alcohol solvent such as methanol. Following this procedure 1α,7α-dimethyl-4-androstene-3,17,19-trione, 7α-methyl-17β-(2'-tetrahydropyranyloxy)-4-androstene-3,19-dione and 17β-hydroxy-7α,17α-dimethyl-4-androstene-3,19-dione are prepared starting with 1α-methyl-4,6-androstadiene-3,17,19-trione, 17β-(2'-tetrahydropyranyloxy)-4,6-androstandiene-3,19-dione and 17β-hydroxy-4,6-androstadiene-3,19-dione. The 3-deoxy-4-androsten-19-ones are also prepared via 19-hydroxy-4-androsten-3-ones. First the 19-hydroxy-4-androsten-3-one is converted to the 3-ethylenethioketal which is then desulfurized with Raney Nickel to the 4-androsten-19-ol. The 19-alcohol is then oxidized to the 4-androsten-19-one employing either the Jones reagent or the Pfitzner-Moffatt procedure described above. In this manner 17β-hydroxy-7,17α-dimethyl-4-androsten-19-one and 17β-hydroxy-6α-methyl-4-androsten-19-one propionate are prepared from 17β,19-dihydroxy-7,17α-dimethyl-4-androsten-3-one and 17β,19-dihydroxy-6α-methyl-4-androsten-3-one 17-propionate.

The mixed ethers, alcohols, esters and ketones on positions 3 and 17 of the basic 4-androsten-19-one nucleus are prepared by selective oxidation, reduction and protection sequences. Thus, a 17β,19-dihydroxy-4-androsten-3-one diester can be selectively hydrolyzed to the 17-monoester by refluxing for one hour in 10% aqueous methanol containing one equivlent sodium bicarbonate. In this manner 17β,19-dihydroxy-4-methyl-4-androsten-31-one dipropionate and 17β,19-dihydroxy-4-androsten-3-one diacetate are converted to 17β,19-dihydroxy-4-methyl-4-androsten-3-one 17-propionate and 17β,19-dihydroxy-4-androstein-3-one 17-acetate, respectively. Similarly, a 4-androstene-3β,17β,19-triol triester can be selectively hydrolyzed to the 3,17 diester by refluxing for one hour in 10% aqueous methanol containing one equivalent sodium bicarbonate. Following this procedure 4-androstene-3β,17β,19-triol triacetate is converted to 4-androstene-3β,17β,19-triol 3,17-diacetate. A 19-hydroxy-4-androstene-3,17-dione can be selectively reduced to 17β,19-dihydroxy-4-androsten-3-one by the action of potassium borohydride in ethanol at −10° to 0° C. for reaction periods of less than 5 hours.

A 4-androstene-3β,17β,19-triol can be selectively oxidized to a 17β,19-dihydroxy-4-androsten-3-one by activated manganese dioxide in an inert solvent such as methylene chloride or chloroform at temperatures below 25° C. Elevated tempertures promote oxidation at position 19. This selective allylic oxidation is also accomplished by the action of dichlorocyanobenzoquinone on the triol in solvents such as dioxane or methylenechloride The preferred temperature is below 25° C. and typical reaction times range from about 1 to about 18 hours. With these reagents 1β-methyl-4-androstene-3β,17β,19-triol and 17β-ethynyl-4-androstene-3β,17β,19-triol are converted to 17β,19-dihydroxy-1β-methyl-4-androsten-3-one and 17β-ethinyl-17β,19-dihydroxy-4-androsten-3-one, respectively.

The 3,17-dihydroxy-4-androsten-19-ones and the diether derivatives are available from the corresponding 19-hydroxy-4-androstene-3,17-dione acylates. Reduction of these compounds with lithium tri-t-butoxyaluminum hydride reduces the 3 and 17-ketones to the β-alcohols without loss of the 19-acylate to furnish 4-androstene-3β,17β,19-triol 19-acylate.

Reduction using a highly hindered lithium or potassium trialkylborohydride such as potassium tri-sec-butylborohydride results in the formation of the 4-androstene-3β,19-diol 19-acylate. Care must be taken during the decomposition of this trialkylborohydride reduction that the reaction temperature does not exceed 25° C. The free hydroxyl groups are now etherified in a manner previously described to form, for example, the 3β,17β,-di-(trialkylsiloxy), di-(tetrahydropyranyloxy), dialkoxy, di(cycloalkenyloxy)-4-androsten-19-ol acylates. The 19-ester is now removed by basic hydrolysis or lithium aluminum hydride reduction. Typical hydrolysis conditions include sodium methoxide in methanol or sodium carbonate in aqueous methanol. Oxidation with Jones reagent or the Pfitzner-Moffatt procedure furnishes the corresponding 19-aldehyde. If the free 3,17-dihydroxy-4-androsten-19-one is desired, the 2-tetrahydropyranyloxy group is the preferred protecting ether as this can be readily removed by mild acid hydrolysis subsequent to oxidation at position 19.

The 3,17-diesters of the 3,17β-dihydroxy-4-androsten-19-ones are prepared by hydrolysis of the 4-androstene-3,17β,19-triol triacylate in 10% aqueous methanol containing one equivalent sodium bicarbonate by heating at reflux temperature for about one hour to form the 3,17-diacylate. Oxidation at position 19 utilizing the aforementioned procedures furnishes the 3,17β-dihydroxy-4-androsten-19-one diacylate.

The 3,17-mixed ethers and esters are available from their corresponding 17β,19-dihydroxy-4-androsten-3-one diacylates. Lithium tri-t-butoxyaluminum hydride reduction yields the 4-androstene-3β,17β,19-triol 17,19-diacylate. The 3-alcohol can be etherified utilizing previously mentioned procedures. The 19-acylate is now selectively hydrolyzed by means of a sodium bicarbonate hydrolysis and the alcohol oxidized to the corresponding aldehyde. This reaction sequence yields 3β,17β-dihydroxy-4-androsten-19-one 3-ether, 17-acylate.

Base hydrolysis with sodium carbonate solution aqueous methanol or sodium methoxide in methanol provides the corresponding 3β,17β-dihydroxy-4-androsten-19-one 3-ether. The hydroxyl group at position 17 can now be etherified with a different group in order to produce the 3,17-mixed ether. By utilizing this procedure, 3β-tetrahydropyranyloxy-17β-hydroxy-4-androsten-19-one 17-acylate can be prepared, which upon removal of the 3β-tetrahydropyranyloxy group using mild acid, results in the preparation of the 3-hydroxy analogue. Reesterification provides the 3,17-mixed ester.

The remaining 17-ethers-3-acylates of 3β,17β-dihydroxy-4-androsten-19-ones are available via 17β,19-dihydroxy-4-androsten-3-one 19-acetate. First the 17-hydroxy group is etherified, followed by a reduction of the 3-ketone with lithium tri-t-butoxy aluminum hydride to the corresponding 3β-alcohol. The alcohol is acylated under conditions previously described and selective hydrolysis of position 19 followed by oxidation yields the desired 3-acylate, 17-ether.

The novel compounds of this invention, represented by formula (I), are useful in modulating the behavior of normal, non-hostile animals when placed in contact with hostile aggressive animals. Hostile aggression in animals can be induced by prolonged isolation of individual animals in the dark. Modulation of the behavioral response in the treated, normally non-hostile animals towards the aggressive animals broadly suggests their use in humans for certain psychasthenic syndromes and related conditions of mental health.

Applicants have made the important discovery that the androst-4-en-19-ones described in formulas (I) and (II) above, enhance the libido of mammals. Illustrative of the term mammals are such species as mice, rats, guinea pigs, rabbits, ferrets, dogs, cats, cows, horses and primates including man. The expression "libido" as used herein refers to the sexual interest and drive in mammals. In higher animals such as primates, including man, the expression "libido" refers, in addition, to certain related psychic attitudes concerned with mental and emotional well-being. Such attitudes are evidenced by an increase in mental activity and alertness, an enhanced ability to perform repetitive mental tasks, and an increase in the creativity, enthusiasm and sociability of the individual. In striking contrast to the androgens previously used for this purpose, these beneficial effects are achieved without any overt concomitant, androgenic, somatic side-effects upon the sex accessory structures.

Libido is generally recognized to be the result of a complex interaction of factors in which genetic, anatomic, neurologic, psychologic and biochemical factors all play prominent roles. The exact mechanism by which the compounds of this invention achieve their effect is not understood except to the extent that it is known to be attributable to some form of biochemical mechanism. Secretions of the endocrine glands are known to affect the psyche. Thus, there is a degree of positive correlation between testosterone blood level changes and dominant or aggressive behavior. Testosterone infusion is also known to improve mental performance in repetitive mental tasks. It has recently been suggested that a dysgenesis of androgen steroids may have a bearing in schizophrenia, cf., Alias, A. G., Lancet, 1248–9, No. 2 (1972).

The fact that libido in both men and women bears a relationship to the endocrine system, and more particularly, to the steroidal hormones associated therewith, has been previously reported, and is clinically recognized. Physicians are often confronted with patients having a variety of symptoms including those of a diminished libido and related psychasthenia, which may be either organic or pyschosomatic in origin. Heretofore, therapy employing the administration of testosterone and it esters, or the orally active 17-methyltestosterone has frequently been employed. Adjunctive androgen therapy is also recommended for the restoration of libido in women with certain gynecologic disturbances and in women who have had oophorectomy and bilateral adrenalectomy. Similarly, androgen therapy has been used to restore libido in impotent men whose impotence has been associated with an endocrine malfunction or insufficiency, as for example, in Addison's disease, castration, diabetes mellitus, eunuchoidism, feminizing interstitial-cell tumors, infantilism and obesity.

Although in some patients such treatment has been effective, it has generally proven to be disappointing due to the physiological side effects of the androgen which soon become apparent. In the female, therapeutic doses of testosterone can produce a virilizing effect including hirsuitism, hoarseness or deepening of the voice and an increase in uterine weight. In the male such symptoms as an increased growth of body hair, in increase in weight of the ventral prostate, enlarged seminal vesicles, increased seminal fluid and sterility have been observed.

The castrated rhesus monkey is a useful primate model in which to demonstrate and observe enhanced libidinous behavior. However, the size and temperament of these animals, plus the expense of maintaining large monkey colonies, makes them unsuitable for ordinary routine screening of large numbers of compounds. The castrated or the castrated-adrenalectomized rat is a more practical and manageable animal model that can be accommodated in the large numbers required for the successful testing of compounds and are the standard experimental animals employed for the evaluation of chemical compounds by those skilled in the art. A high degree of correlation exists in the data obtained using the castrated rat and the castrated monkey.

Administration of the androst-4-en-19-ones above to castrated or castrated-adrenalectomized rats results in both an increase in the number and frequency of mounts, intromissions and ejaculations as compared with castrated control animals. Notably, there is observed a decrease in the refractory period following emission. This refractory or post-ejaculatory period for the rat refers to the time period following emission and prior to remounting. During this period the male rat is sexually inert and will even resist any sexual advances made by the female. Many observers feel the refractory period provides a more realistic evaluation of libido enhancement. On necrospy examinations of the secondary sex organs of the animals treated, i.e., the ventral prostate and seminal vesicles, fail to show any overt peripheral, somatic effects normally associated with androgen administration, and more particularly associated with the administration of testosterone.

The compounds of the present invention can be administered in various unit dosage forms including tablets or lozenges for purpose of absorption through the buccal mucosa. The active ingredient may be enclosed in hard or soft gelatin capsules, or it may be compressed directly into tablets, or they may be incorporated with other pharmaceutical excipients and inert diluents and used in the form of troches, elixirs, suspensions, syrups, wafers, chewing gum and the like. Such compositions and preparations can contain anywhere from 0.1 milligram to about 3 grams of active compound per dosage unit form. Preferably an amount of active ingredient ranging from 0.1 milligram to 500 milligrams is employed per dosage unit. The tablets, troches, pills and capsules may also contain the following pharmaceutical excipients: a binder such as gum tragacanth, acacia, corn starch or gelatin; a diluent such as dicalcium phosphate; a disintegrating agent such as corn starch, potato starch, alginic acid; a lubricant such as magnesium stearate; a sweetening agent such as sucrose, lactose or saccharin, and flavoring agents such as peppermint, oil of wintergreen of cherry flavoring. Various other materials may also be present as coatings or to otherwise modify the physical form of the dosage unit, as for example, shellac-coated tablets or capsules and sugar-coated tablets. Syrups or elixirs may contain the active ingredients, surcose as a sweetening agent, methyl and propyl parabens as preservatives, and a suitable dye of flavoring agent.

Parental fluid dosage forms or injectable forms including those which can be administered by a jet gun are prepared by a utilizing the active ingredient in a sterile liquid vehicle such as water or saline solution. Compositions having the desired clarity, stability and adaptability for parenteral use are obtained by dissolving from about 0.1 milligram to about 3 grams of the active ingredient in a vehicle consisting of a mixture of nonvolatile, liquid polyethylene glycols which are soluble in water and organic liquids and which have molecular weights ranging from about 200 to about 1,500. Such solutions may advantageously contain suspending agents, such as sodium carboxymethylcellulose, methylcellulose, polyvinyl pyrrolidone or polyvinyl alcohol. In the case of injectable forms, they may also contain preservatives in the nature of bactericidal and fungicidal agents, as for example, parabens, benzyl alcohol, phenol or thimersol. If desired, isotonic agents are included such as various sugar or sodium chloride. Adjuvants include local anesthetics and stabilizing or buffering agents may also be usefully employed.

The active ingredient can also be compressed into pellets or small cylinders and implanted subcutaneously or intramuscularly as depot injections or implants. Implants may employ inert materials such as biodegradable polymers or synthetic silicones, as for example, Silastic, silicone rubber manufactured by the Dow-Corning Corporation. Implanation results in a slow but, nevertheless, predictable rate of absorption from the site of implantation.

The following preparations and examples are illustrative of the novel compounds of the present invention and their compositions but are not to be construed as necessarily limiting the scope thereof.

EXAMPLE 1

17β,19-DIHYDROXY-1,4-ANDROSTADIEN-3-ONE DIPROPIONATE

17β,19-Dihydroxy-4-androsten-3-one dipropionate and dichlordicyanobenzoquinone are refluxed in anhydrous dioxane for about 48 hours. The mixture is cooled and filtered and the filtrate concentrated under vacuum. Methylenechloride is added and the mixture filtered. The filtrate is washed well with water, dried over sodium sulfate and the solvent removed. Chromatography on silica gel and elution with methylenechloride results in a solid which is crystallized from acetone-hexane to yield the desired 17β,19-dihydroxy-1,4-androstadien-3-one dipropionate.

Following essentially the same procedure and substituting 17β,19-dihydroxy-17β-methyl-4-androsten-3-one dipropionate, 19-hydroxy-4-androstene-3,17-dione propionate, 17β,19-dihydroxy-7β-methyl-4-androsten-3-one dipropionate, and 17β,19-dihydroxy-6β,17β-dimethyl-4-androsten-3-one dipropionate for the 17β,19-dihydroxy-4-androsten-3-one dipropionate above results in the formation of 17β,19-dihydroxy-17β-methyl-1,4-androstadien-3-one dipropionate, 19-hydroxy-1,4-androstadiene-3,17-dione propionate, 17β,19-dihydroxy-7α-methyl-1,4-androstadien-3-one dipropionate and 17β,19-dihydroxy-6α,17α-dimethyl-1,4-androstadien-3-one dipropionate, respectively.

EXAMPLE 2

17β,19-DIHYDROXY-1α-METHYL-4-ANDROSTEN-3-ONE DIPROPIONATE

A solution of lithium dimethylcopper is prepared under nitrogen by the addition of 1.6 M etheral methyllithium to an ether slurry of cuprous iodide at 0° C. The solution is stirred at 0° for 20 minutes and a solution of 17β,19-dihydroxy-1,4-androstadien-3-one dipropionate in anhydrous tetrahydrofuran is added slowly and stirred for about 30 minutes. The mixture is poured onto a saturated aqueous ammonium chloride solution, benzene added and the resulting mixture filtered through diatomaceous earth. The organic layer is washed with aqueous ammonium chloride, water, dried over mangesium sulfate and evaporated to dryness. The residue which remains is passed through a silica gel column and eluted with benzene. Recrystallization of the evaporated eluate from hexane yields 17β,19-dihydroxy-1α-methyl-4-androsten-3-one dipropionate.

Substituting 17β,19-dihydroxy-17α-methyl-1,4-androstadien-3-one dipropionate, 19-hydroxy-1,4-androstadiene-3,17-dione propionate, 17β,19-dihydroxy-7α,-methyl-1,4-androstadien-3-one dipropionate and 17β,19-dihydroxy-6α,17α-dimethyl-1,4-androstadien-3-one dipropionate for the 17β,19-dihydroxy-1,4-androstadien-3-one dipropionate above results in the formation of 17β,19-dihydroxy-1α,17α-dimethyl-4-androsten-3-one dipropionate, 19-hydroxy-1α-methyl-4androstene-3,17-dione propionate, 17β,19-dihydroxy-1α,7α-dimethyl-androst-4-en-3-one dipropionate and 17β,19-dihydroxy-1α,6α,17α-trimethyl-4-androsten-3-one dipropionate, respectively.

EXAMPLE 3

17β,19-DIHYDROXY-1α-METHYL-4-ANDROSTEN-3-ONE

A solution of 17β,19-dihydroxy-1α,-methyl-4-androsten-3-one dipropionate in methanol is refluxed for about two hours with aqueous sodium carbonate. The solvent is removed and the residue dissolved in chloroform. The chloroform extract is washed well with water, dried over magnesium sulfate and evaporated under vacuum. The residue which remains is crystallized from acetonitrile to yield 17β,19-dihydroxy-1α-methyl-4-androsten-3-one.

Substituting 17β,19-dihydroxy-1α,17α-dimethyl-4-androsten-3-one dipropionate, 19-hydroxy-1α-methyl-4-androstene-3,17-dione propionate, 17β,19-dihydroxy-1α,7α-dimethyl-4-androsten-3-one dipropionate and 17β,19-dihydroxy-1α,6α,17α-trimethyl-4-androsten-3-one dipropionate for the 17β,19-dihydroxy-1α-methyl-4-androsten-3-one dipropionate above results in the formation of 17β,19-dihydroxy-1α,17α-dimethyl-4-androsten-3-one, 19-hydroxy1α-methyl-4-androstene-3,17-dione, 17β,19-dihydroxy-1α,7α-dimethyl-4-androsten-3-one and 17β,19-dihydroxy-1α,6α,17α-trimethyl-4-androsten-3-one, respectively.

EXAMPLE 4

17β,19-DIHYDROXY-1α-METHYL-4-ANDROSTEN-3-ONE 17-PROPIONATE

To a solution of 17β,19-dihydroxy-1α-methyl-4-androsten-3-one dipropionate in 10% aqueous methanol is added one equivalent sodium bicarbonate and the solution is heated at its reflux temperature for about one hour. Methanol is removed under vacuum to half volume, and the concentrate is poured onto water. The solid which forms is filtered, air dried, and crystallized from hexane to yield 17β,19-dihydroxy-1α-methyl-4-androsten-3-one 17-propionate.

Substituting 17β,19-dihydroxy-1α,17α-dimethyl-4-androsten-3-one dipropionate, 17β,19-dihydroxy-1α,-7α-dimethyl-4-androsten-3-one dipropionate, and 17β,19-dihydroxy-1α,6α,17α-trimethyl-4-androsten-3-one dipropionate for the 17β,19-dihydroxy-1α-methyl-4-androsten-3-one dipropionate above results in the preparation of 17β, 19-dihydroxy-1α,17α-dimethyl-4-androsten-3-one 17-propionate, 17β,19-dihydroxy-1α,7α-dimethyl-4-androsten-3-one 17-propionate and 17β,19-dihydroxy-1α,6α,17α-trimethyl-4-androsten-3-one 17-propionate.

EXAMPLE 5

1α-METHYL-4-ANDROSTENE-3,17,19-TRIONE

To a solution of 17β,19-dihydroxy-1α-methyl-4-androsten-3-one in acetone at 20° C. is added 2 equivalents of Jones Reagent with stirring. After 15 minutes the upper acetone layer is decanted and poured onto ice water and stirred for an additional 30 minutes. The precipitate which forms is filtered, washed with water and dissolved in ether. The ether solution is dried over magnesium sulfate and concentrated under reduced pressure. The residue is crystallized from acetone-hexane to yield 1α-methyl-4-androstene-3,17,19-trione.

Substituting 17β,19-dihydroxy-1α,17α-dimethyl-4-androsten-3-one, 19-hydroxy-1α-methyl-4-androstene-3,17-dione, 17β,19-dihydroxy-1α,7α-dimethyl-4-androsten-3-one and 17β,19-dihydroxy-1α,6α,17α-trimethyl-4-androsten-3-one for the 17β,19-dihydroxy-1α-methyl-4-androsten-3-one above results in the preparation of 17β-hydroxy-1α,17α-dimethyl-4-androstene-3,19-dione, 1α-methyl-4-androstene-3,17,19-trione, 1α,7α-dimethyl-4-androstene-3,17,19-trione and 17β-hydroxy-1α,6α,17α-trimethyl-4-androstene-3,19-dione, respectively.

EXAMPLE 6

17β-HYDROXY-1α-METHYL-4-ANDROSTENE-3,19-DIONE PROPIONATE

A solution of 17β,19-dihydroxy-1α-methyl-4androsten-3one 17-propionate in acetone at 20° C. is titrated with one equivalent of Jones Reagent with stirring. After approximately 15 minutes the upper acetone layer is decanted and poured onto ice water with vigorous stirring. The precipitate is removed by filtration, washed well with water, and dissolved in ether. The ether solution is dried over magnesium sulfate and the ether removed under vacuum. The residue is crystallized from acetone-hexane to yield 17β-hydroxy-1α-methyl-4-androstene-3,19-dione propionate.

Substituting 17β,19-dihydroxy-1α,17α-dimethyl-4-androsten-3-one 17-propionate, 17β,19-dihydroxy-1α,7α-dimethyl-4-androsten-3-one 17-propionate and 17β,19-dihydroxy-1α,6α,17α-trimethyl-4-androsten-3one propionate for the 17β,19-dihydroxy-1α-methyl-4-androsten-3-one 17-propionate above results in the preparation of 17β-hydroxy-1α,17α-dimethyl-4-androstene-3,19-dione 17-propionate, 17β-hydroxy-1α,7α-dimethyl-4-androstene-3,19-dione 17-propionate and 17β-hydroxy-1α,6α,17α-trimethyl-4-androstene-3,19-dione 17-propionate, respectively.

EXAMPLE 7

1α-METHYL-4-ANDROSTENE-17β,19-DIOL

17β,19-Dihydroxy-1αmethyl-4-androsten-3-one in acetic acid is treated with ethanedithiol and p-toluenesulfonic acid. After standing about 4 hours at room temperature, the solution is poured onto water and the mixture extracted with methylenechloride. The methylene-chloride extract is washed well with water, sodium hydroxide solution, water, dried over sodium sulfate and evaporated under reduced pressure to leave 17β,19-dihydroxy-1α-methyl-4-androsten-3-one 3-ethylenethioketal which is recrystallized once from acetone-hexane.

Raney nickel is added to a solution of the above 17β,19-dihydroxy-1α-methyl-4-androsten-3-one 3-ethylenethioketal in methanol and the resulting suspension is refluxed for about 4 hours with rapid stirring. The suspension is cooled, filtered and the solvent evaporated. The residue is chromatographed on silica gel and eluted with methylenechloride. Recrystallization from acetone-hexane yields 1α-methyl4-androstene-17β,19-diol.

Substituting 17β,19-dihydroxy-4-androsten-3-one for the 17β,19-dihydroxy-1α-methyl-4-androsten-3-one above results in the preparation of 4-androstene-17β,19-diol.

EXAMPLE 8

1α-METHYL-4-ANDROSTENE-17β,19-DIOL DIPROPIONATE

1α-Methyl-4-androstene-17β,19-diol is dissolved in a mixture of pryidine and propionic anhydride and stirred overnight under nitrogen at room temperature.

Ethanol is added and stirring continued for another 2 hours. The solvents are removed under vacuum and the residue recrystallized from hexane to yield 1α-methyl-4-androstene-17β,19-diol dipropionate.

Substituting 4-androstene-17β,19-diol for the 1α-methyl-4-androstene-17β,19-diol above results in the formation of 4-androstene-17β,19-diol dipropionate.

EXAMPLE 9

1α-METHYL-4-ANDROSTENE-17β,19-DIOL 17-PROPIONATE

1α-Methyl-4-androstene-17β,19-diol dipropionate is dissolved in a 10% aqueous methanol solution and one equivalent of sodium bicarbonate is added. The solution is stirred and heated at its reflux temperature for one hour and poured onto ice water with vigorous stirring. The precipitate is removed by filtration, air dried and crystallized from hexane to yield 1α-methyl-4-androstene-17β,19-diol 17-propionate.

Substituting 4-androstene-17β,19-diol dipropionate for the 1α-methyl-4-androstene-17β,19-diol dipropionate above results in the preparation of 4-androstene-17β,19-diol 17-propionate.

EXAMPLE 10

1α-METHYL-4-ANDROSTENE-17,19-DIONE

1α-Methyl-4-androstene-17β,19-diol is dissolved in dimethylformamide at 40° C. and two equivalents of Jones Reagent are added all at once. The mixture is stirred for about 5 hours at 40° C., cooled and a 1% aqueous sodium sulfite solution is added. After several hours the crystals which form are collected by filtration, thoroughly washed with water and air dried. Crystallization from hexane yields the desired 1α-methyl-4-androstene-17,19-dione.

In the same manner, substituting 4-androstene-17β,19-diol for the 1α-methyl-4-androstene-17β,19-diol above results in the preparation of 4-androstene-17,19-dione.

EXAMPLE 11

17β-HYDROXY-1α-METHYL-4-ANDROSTEN-19-ONE PROPIONATE

To a solution of 1α-methyl-4-androstene-17β,19-diol 17-propionate in dimethylformamide at 40° C. is rapidly added one equivalent of Jones Reagent. The solution is stirred for about 5 hours at 40° C., cooled and a 1% aqueous sodium sulfite solution is added. The precipitate is collected, washed well with water and crystallized from hexane to yield 17β-hydroxy-1α-methyl-4-androsten-19-one propionate.

Substituting 4-androstene-17β,19-diol 17-propionate for the 17β-hydroxy-1α-methyl-4-androsten-19-one propionate above results in the preparation of 17β-hydroxy-4-androsten-19-one propionate.

EXAMPLE 12

17β-HYDROXY-1α-METHYL-4-ANDROSTEN-19-ONE

A solution of 17β-hydroxy-1α-methyl-4-androsten-19-one propionate and sodium carbonate in aqueous methanol is refluxed under nitrogen for approximately 2 hours and poured onto water. The oil which forms is extracted with ether. The ether extract is washed with water, dried over sodium sulfate, and concentrated under reduced pressure. The residue which remains is eluted from silica gel with benzene and crystallized from hexane to yield 17β-hydroxy-1α-methyl-4-androsten-19-one.

Substituting 17β-hydroxy-4-androsten-19-one propionate for the 17β-hydroxy-1α-methyl-4-androsten-19-one propionate above results in the preparation of 17β-hydroxy-4-androsten-19-one.

EXAMPLE 13

1α-METHYL17β-TRIMETHYLSILOXY-4-ANDROSTEN-19-ONE

A mixture of 17β-hydroxy-1α-methyl-4-androsten-19-one, trimethylchlorosilane and pyridine is refluxed in benzene for a period of about 18 hours. The suspension is filtered and the benzene removed under vacuum. The resulting oil is eluted from a silica gel chromatograph with benzene and crystallized from hexane to yield 1α-methyl-17β-trimethylsiloxy-4-androsten-19-one.

Substituting 17β-hydroxy-4-androsten-19-one for the 17β-hydroxy-1α-methyl-4-androsten-19-one above results in the formation of 17β-trimethylsiloxy-4-androsten-19-one.

EXAMPLE 14

17β-(1'-ETHOXY-1'-CYCLOHEXYLOXY)-1α-METHYL-4-ANDROSTEN-19-ONE

A solution of 17β-hydroxy-1α-methyl-4-androsten-19-one in anhydrous dioxane is treated at room temperature with pyridine p-toluenesulfonate and cyclohexanone ethyl enolether. A precipitate forms on standing overnight which is filtered and crystallized from methanol to yield 17β-(1'-ethoxy-1'-cyclohexyloxy)-1α-methyl-4-androsten-19-one.

Substituting 17β-hydroxy-4-androsten-19-one for the 17β-hydroxy-1α-methyl-4-androsten-19-one above results in the preparation of 17β-(1'-ethoxy-1'-cyclohexyloxy)-4-androsten-19-one.

EXAMPLE 15

17β-(1'-CYCLOHEXENYLOXY)-1α-METHYL-4-ANDROSTEN-19-ONE

17β(1'-Ethoxy-1'-cyclohexyloxy)-1α-methyl-4-androsten-19-one prepared above is dissolved in dimethylformamide containing a drop of pyridine. The solution is heated at 150° C. for 1 hour allowing the alcohol which forms to distill. The solvent is removed under vacuum and the residue crystallized from methanol to yield 17β-(1'-cyclohexenyloxy)-1α-methyl-4-androsten-19-one.

Substituting 17β-(1'-ethoxy-1'-cyclohexyloxy)-4-androsten-19-one for the 17β-(1'-ethoxy-1'-cyclohexyloxy)-1α-methyl-4-androsten-19-one above results in the formation of 17β-(1'-cyclohexenyloxy)-4-androsten-19-one.

EXAMPLE 16

1α-METHYL-17β-(2'-TETRAHYDROPYRANYLOXY)-4-ANDROSTEN-19-ONE

To a stirred solution of 17β-hydroxy-1αmethyl-4-androsten-19-one and p-toluenesulfonic acid in anhydrous dioxane is slowly added dihydropyran. After 5 minutes, methanolic ammonia is added until the solution becomes slightly basic. The solvent is removed under vacuum and the residue is dissolved in methylene chloride. The solution is extracted with a solution of aqueous sodium bicarbonate, dried over sodium sulfate, and concentrated under vacuum. The residue is crystallized from pentane to yield 1α-methyl-17β-(2'-tetrahydropyranyloxy)-4-androsten-19-one.

Substituting 17β-hydroxy-4-androsten-19-one for the 17β-hydroxy-1α-methyl-4-androsten-19-one above results in the preparation of 17β-(2'-tetrahydropyranyloxy)-4-androsten-19-one.

EXAMPLE 17

1β,2β-METHYLENE-4-ANDROSTENE-3,17-DIONE

To a solution of potassium t-butoxide in dimethylsulfoxide at 25° C. under nitrogen is added 1,4-androstadiene-3,17-dione in dimethylsulfoxide with stirring. After a period of 15 minutes the mixture is poured onto a cold aqueous ammonium chloride solution. The solid is rapidly filtered, washed well with water and dissolved in ether. The ether solution is washed with water, dried over sodium sulfate and evaporated at room temperature to yield 1,5-androstadiene-3,17-dione.

A tetrahydrofuran solution of the 1,5-androstadiene-3,17-dione so prepared is added to a solution of lithium tri-t-butoxyaluminum hydride in tetrahydrofuran. After stirring overnight at room temperature, an aqueous solution of potassium sodium tartrate is added with stirring to form a readily filterable white solid. The reaction mixture is filtered. The filtrate is dried over magnesium sulfate, the solvent removed and the residue is recrystallized from acetone to yield 1,5-androstadiene-3β,17β-diol.

To a stirred solution of the 1,5-androstadiene-3β,17β-diol so prepared in a mixture of dry ether and glyme is added zinc-copper couple and methylene iodide. The mixture is refluxed for a period of about 4 hours, cooled to room temperature, diluted with ether and filtered. The filtrate is washed with an aqueous sodium chloride solution, water and dried over anhydrous magnesium sulfate. The ether is removed under reduced pressure and the residue crystallized from acetone-hexane to yield 1β,2β-methylene-5-androstene-3β,17β-diol.

The 1β,2β-methylene-5-androstene-3β,17β-diol prepared in this manner is dissolved in acetone and Jones Reagent added until a persistent yellow-orange color appears. After stirring at room temperature for 10 minutes the mixture is poured onto ice-water and the precipitate is dissolved in a solution of sodium methoxide in methanol and stirred about 30 minutes at room temperature. The methanol is removed and the residue triturated with water. The filtered solid is crystallized from acetone to yield 1β,2β-methylene-4-androstene-3,17-dione.

Following essentially the same procedure and substituting 7α-methyl-1,4-androstadiene-3,17-dione and 6α-methyl-1,4-androstadiene-3,17-dione for the 1,4-androstadiene-3,17-dione above results in the preparation of 7α-methyl-1β,2β-methylene-4-androstene-3,17-dione and 6α-methyl-1β,2β-methylene-4-androstene-3,17-dione.

EXAMPLE 18

1β-METHYL-4-ANDROSTENE-3,17-DIONE

1β,2β-Methylene-4-androstene-3,17-dione, zinc powder, and acetic acid are refluxed for about one hour. Benzene is added, the suspension filtered and the filtrate taken to dryness under vacuum. The residue is chromatographed on silica gel and eluted with methylenechloride. Recrystallization from acetone-hexane yields 1β-methyl-4-androstene-3,17-dione.

Substituting 7α-methyl-1β,2β-methylene-4-androstene-3,17-dione and 6α-methyl-1β,2β-methylene-4-androstene-3,17-dione for the 1β,2β-methylene-4-androstene-3,17-dione above results in the preparation of 1β,7α-dimethyl-4-androstene-3,17-dione and 1β,6α-dimethyl-4-androstene-3,17-dione, respectively.

EXAMPLE 19

1β-METHYL-5-ANDROSTENE-3β,17β-DIOL, DIACETATE

To a solution of potassium t-butoxide in dimethylsulfoxide at 25° C. under nitrogen is added 1β-methyl-4-androstene-3,17-dione in dimethylsulfoxide with stirring. After 15 minutes the mixture is poured onto cold aqueous ammonium chloride. The solid is rapidly filtered, washed well with water and dissolved in ether. The ether is washed with water, dried over sodium sulfate and removed at room temperature to yield 1β-methyl-5-androstene-3,17-dione.

A tetrahydrofuran solution of 1β-methyl-5-androstene-3,17-dione so prepared is added under nitrogen to a solution of lithium tri-t-butoxyaluminum hydride in tetrahydrofuran. After stirring at room temperature for about 18 hours, an aqueous solution of potassium sodium tartrate is added with stirring to form a readily filterable white solid. The reaction mixture is filtered, the filtrate dried over magnesium sulfate, and the solvent removed from the filtrate. The residue which is crystallized from acetone-hexane yields 1β-methyl-5-androstene-3β,17β-diol.

The 1β-methyl-5-androstene-3β,17β-diol prepared in this manner is dissolved in acetic anhydride and pyridine and maintained at room temperature for about 20 hours. The solvent is removed under vacuum and the residue recrystallized from hexane to yield 1β-methyl-5-androstene-3β,17β-diol diacetate.

Substituting 1β,7α-dimethyl-4-androstene-3,17-dione and 1β,6α-dimethyl-4-androstene-3,17-dione for the 1β-methyl-4-androstene-3,17-dione above results in the preparation of 1β,7α-dimethyl-5-androstene-3β,17β-diol diacetate and 1β,6-dimethyl-5-androstene-3β,17β-diol diacetate.

EXAMPLE 20

5α-BROMO-1β-METHYLANDROSTANE-3β,6β,17β-TRIOL 3,17-DIACETATE

A solution of 1β-methyl-5-androstene-3β,17β-diol diacetate in ether is cooled to −5° C.. in an ice-methanol bath and a solution of aqueous perchloric acid added followed by the addition of N-bromoacetamide. Stirring at −5° C. is continued for approximately two hours and water is added. The ether layer which separates is washed with water until neutral and concentrated to a small volume at room temperature. The product which forms is filtered and crystallized from acetone-hexane to yield 5α-bromo-1β-methylandrostane-3β,6β,17β-triol 3,17-diacetate.

Substituting 1β,7α-dimethyl-5-androstene-3β,17β-diol diacetate and 1β,6-dimethyl-5-androstene-3β,17β-diol diacetate for the 1β-methyl-5-androstene-3β,17β-diol diacetate above results in the preparation of 5α-bromo-1β,7α-dimethyl-androstane-3β,6β,17β-triol 3,17-diacetate and 5α-bromo-1β,6-dimethyl-androstane-3β,6β,17β-triol 3,17-diacetate.

EXAMPLE 21

5α-BROMO-1β-METHYL-6β,19-OXIDOANDROSTANE-3β,17β-DIOL DIACETATE

A stirred suspension of lead tetraacetate and calcium carbonate in cyclohexane is refluxed for 30 minutes and iodine and 5α-bromo-1β-methyl-androstane-3β,6β,17β-triol 3,17-diacetate are added. The stirred mixture is irradiated with a 600 Watt lamp which maintains the mixture as its reflux temperature. After the iodine color has disappeared the mixture is cooled, filtered and washed with ether. The filtrates are combined and concentrated to 1/5 volume, washed with a 10% sodium thiosulfate solution and water, dried over magnesium sulfate and evaporated under reduced pressure to yield a semi-solid residue which when crystallized from acetone-hexane yields 5α-bromo-1β-methyl-6β,19-oxidoandrostane-3β,17β-diol diacetate.

Substituting 5α-bromo-1β,7α-dimethyl-androstane-3β,6β,17β-triol 3,17-diacetate and 5α-bromo-1β,6-dimethyl-androstane-3β,6β,17β-triol 3,17-diacetate for the 5α-bromo-1β-methyl-androstane-3β,6β,17β-triol 3,17-diacetate above results in the preparation of 5α-bromo-1β,7α-dimethyl-6β,19-oxidoandrostane-3β,17β-diol diacetate and 5α-bromo-1β,6-dimethyl-6β,19-oxidoandrostane-3β,17β-diol diacetate.

EXAMPLE 22

5α-BROMO-1β-METHYL-6β,19-OXIDOANDROSTANE-3β,17β-diol

To a solution of 5α-bromo-1β-methyl-6β,19-oxidoandrostane-3β,17β-diol diacetate in methanol is added a 5% aqueous potassium carbonate solution. The mixture is refluxed for about 3 hours, the methanol removed by distillation, and water added. The solid which forms is filtered and crystallized from aqueous methanol to yield 5α-bromo-1β-methyl-6β,19-oxidoandrostane-3β, 17β-diol.

Substituting 5α-bromo-1β,7α-dimethyl-6β,19-oxidoandrostane-3β,17β-diol diacetate and 5α-bromo-1β,6-dimethyl-6β,19-oxidoandrostane-3β,17β-diol diacetate for the 5α-bromo-1β-methyl-6β,19-oxidoandrostane-3β,17β-diol diacetate above results in the preparation of 5α-bromo-1β,7α-dimethyl-6β,19-oxidoandrostane-3β,17β-diol and 5α-bromo-1β,6-dimethyl-6β,19-oxidoandrostane-3β,17β-diol.

EXAMPLE 23

5α-BROMO-1β-METHYL-6β,19-OXIDOANDROSTANE-3,17-DIONE

5α-Bromo-1β-methyl-6β,19-oxidoandrostane-3β,17β-diol is dissolved in acetone and Jones Reagent added until a persistent yellow-orange color appears. Stirring is continued for an additional 30 minutes and the solution poured onto water. The solid is filtered and recrystallized from acetone-hexane to yield 5α-bromo-1β-methyl-6β,19-oxidoandrostane-3,17-dione.

Substituting 5α-bromo-1β,7α-dimethyl-6β,19-oxidoandrostane-3β,17β-diol and 5α-bromo-1β,6-dimethyl-6β,19-oxidoandrostane-3β,17β-diol for the 5α-bromo-1β-methyl-6β,19-oxidoandrostane-3β,17β-diol above results in the preparation of 5α-bromo-1β,7α-dimethyl-6β,19-oxidoandrostane-3,17-dione and 5α-bromo-1β,6-dimethyl-6β,19-oxidoandrostane-3,17-dione.

EXAMPLE 24

19-HYDROXY-1β-METHYL-4-ANDROSTENE-3,17-DIONE

Zinc powder is added to a solution of 5α-bromo-1β-methyl-6β,19-oxidoandrostane-3,17-dione in ethanol and the mixture heated at its reflux temperature with stirring for a period of about 3 hours. The suspension is filtered and the zinc cake washed with hot ethanol. Removal of the solvent from the combined filtrates affords a residue which is recrystallized from acetone-hexane to yield 19-hydroxy-1β-methyl-4-androstene-3,17-dione.

Substituting 5α-bromo-1β,7α-dimethyl-6β,19-oxidoandrostane-3,17-dione and 5α-bromo-1β,6-dimethyl-6β,19-oxidoandrostane-3,17-dione for the 5α-bromo-1β-methyl-6β,19-oxidoandrostane-3,17-dione above results in the preparation of 19-hydroxy-1β,7α-dimethyl-4-androstene-3,17-dione and 19-hydroxy-1β,6α-dimethyl-4-androstene-3,17-dione.

EXAMPLE 25

1β-METHYL-4-ANDROSTENE-3,17,19-TRIONE

19-Hydroxy-1β-methyl-4-androstene-3,17-dione is added to a mixture containing dimethylsulfoxide, benzene, pyridine, trifluoroacetic acid and N,N'-dicyclohexylcarbodiimide and allowed to react for 12 hours at room temperature. Ethylacetate is added and the reaction mixture is filtered. The filtrate is extracted with a solution of sodium bicarbonate, water and dried over magnesium sulfate. After evaporation of the solvent under reduced pressure, the residue is crystallized from ether to yield 1β-methyl-4-androstene-3,17,19-trione.

Substituting 19-hydroxy-1β,7α-dimethyl-4-androstene-3,17-dione and 19-hydroxy-1β,6α-dimethyl-4-androstene-3,17-dione for the 19-hydroxy-1β-methyl-4-androstene-3,17-dione above results in the preparation of 1β,7α-dimethyl-4-androstene-3,17,19-trione and 1β,6α-dimethyl-4-androstene-3,17,19-trione.

EXAMPLE 26

17β,19-DIHYDROXY-4,6α,17α-TRIMETHYL-4-ANDROSTEN-3-one

A mixture of 17β,19-dihydroxy-6α,17α-dimethyl-4-androsten-3-one, thiophenol, 40% aqueous formaldehyde, triethylamine and ethanol is heated under reflux for a period of about 48 hours. The cooled solution is poured into an aqueous sodium hydroxide solution and the product isolated by ether extraction. The ether extract is washed with water and dried over magnesium sulfate. The residue left after evaporation of the ether is triturated with hexane to remove any condensation products present which are derived from the thiophenol and formaldehyde. The 17β,19-dihydroxy-6α-methyl-4-phenylthiomethyl-4-androsten-3-one so obtained is desulfurized by dissolving in acetone and added to a suspension of Raney Nickel in refluxing acetone. The mixture is heated at its reflux temperature while stirring for about 5 hours. The hot solution is filtered and the nickel washed with boiling ethanol and water. The combined filtrates are concentrated under vacuum whereupon the product separates as a solid. Recrystallization of this solid from acetone-hexane yields 17β,19-dihydroxy-4,6α,17α-trimethyl-4-androsten-3-one.

EXAMPLE 27

17β-HYDROXY-4,6α,17α-TRIMETHYL-4-ANDROSTENE-3,19-DIONE

17β,19-Dihydroxy-4,6α,17α-trimethyl-4-androsten-3-one is added to a mixture of dimethylsulfoxide, benzene, pyridine, trifluoroacetic acid and N,N'-dicyclohexylcarbodiimide and stirred at room temperature for about 12 hours. Ethylacetate is added and the mixture filtered. The filtrate is washed with water, dried over magnesium sulfate and concentrated under vacuum. Crystallization of the residue from ether yields 17β-hydroxy-4,6α,17α-trimethyl-4-androstene-3,19-dione.

EXAMPLE 28

17β-HYDROXY-4,6α,17α-TRIMETHYL-4-ANDROSTENE-3,19-DIONE ACETATE

17β-Hydroxy-4,6α,17α-trimethyl-4-androstene-3,19-dione, pyridine and acetic anhydride are stirred for 48 hours at room temperature and poured onto ice water. The solid which forms is removed by filtration and crystallized from ether-hexane to yield 17β-hydroxy-4,6α,17α-trimethyl-4-androstene-3,19-dione acetate.

EXAMPLE 29

17β,19-DIHYDROXY-4,17α-DIMETHYL-4-ANDROSTEN-3-ONE

A solution of 17β,19-dihydroxy-17α-methyl-4-androsten-3-one in t-butanol is heated to boiling and added to a boiling solution of potassium t-butoxide in t-butanol. Methyl chloride in t-butanol is added slowly. The solution is cooled, acidified with concentrated hydrochloric acid, and diluted with water. The excess t-butanol is removed under vacuum and the aqueous layer extracted with ethylacetate. The ethylacetate extract is washed with water, dried over magnesium sulfate and evaporated in vacuo. The residue is chromatographed on silica gel and eluted with ethylacetate. The eluant is evaporated and the residue crystallized from acetonitrile to yield 17β,19-dihydroxy-4,17α-dimethyl-4-androstene-3-one.

EXAMPLE 30

17β-HYDROXY-4,17α-DIMETHYL-4-ANDROSTENE-3,19-DIONE

To a solution of 17β,19-dihydroxy-4,17α-dimethyl-4-androsten-3-one in acetone at 25° C. is added with stirring one equivalent of Jones reagent After standing for a period of about 15 minutes the upper acetone layer is decanted and poured onto ice water with vigorous stirring. The precipitate which forms is removed by suction filtration, washed well with water and dissolved in ether. The ether solution is dried over magnesium sulfate and the ether removed in vacuo. The residue is crystallized from acetone-hexane to yield 17β-hydroxy-4,17α-dimethyl-4-androstene-3,19-dione.

EXAMPLE 31

5α,6α-EPOXY-17α-METHYLANDROSTANE-3β,17β,19-TRIOL 3,19-DIACETATE

A solution of 17α-methyl-5-androstene-3β,17β,19-triol 3,19-diacetate in chloroform is chilled to 0° C. and treated with m-chloroperbenzoic acid in chloroform precooled to 0° C. The mixture is stirred and allowed to warm to room temperature. After standing for a period of 48 hours the solution is washed with solutions of 10% sodium sulfite, sodium thiosulfate, sodium bicarbonate, and finally with water. The chloroform extract is dried over magnesium sulfate and evaporated in vacuo. The remaining residue is crystallized from methanol to yield 5α,6α-epoxy-17α-methylandrostane-3β,17β,19-triol 3,19-diacetate.

EXAMPLE 32

6β,17α-DIMETHYLANDROSTANE-3β,5α,17β,19-TETROL

Ethereal methylmagnesium bromide is added slowly to a stirred solution of 5α,6α-epoxy-17α-methylandrostane-3β,17β,19-triol in tetrahydrofuran The solution is heated at its reflux temperature for about 24 hours, cooled, and poured onto a saturated aqueous ammonium chloride solution. The mixture is extracted with ethylacetate, washed with brine, dried over magnesium sulfate and the solvent removed under reduced pressure. The residue which remains is crystallized from ethylacetate to yield 6β,17α-dimethylandrostane-3β,5α,17β,19-tetrol.

EXAMPLE 33

17β-HYDROXY-6α,17α-DIMETHYL-4ANDROSTENE-3,19-DIONE

6β,17α-Dimethylandrostane-3β,5α,17β,19-tetrol is dissolved in acetone and two equivalents of Jones Reagent added with stirring. After about 15 minutes the reaction mixture is poured onto water. The mixture is stirred for 30 minutes and the solid which forms is filtered and dissolved in methanol containing sodium hydroxide. After 2 hours the methanol is removed at room temperature and the residue which remains is triturated with water. Recrystallization of this residue from acetone-water yields 17β-hydroxy-6α,17α-dimethyl-4-androstene-3,19-dione.

EXAMPLE 34

6α,17α-DIMETHYL-4-ANDROSTENE-3β,17β,19-TRIOL

Sodium borohydride is added under nitrogen with stirring to a solution of 17β-hydroxy-6α,17α-dimethyl-4-androstene-3,19-dione in methanol. After standing 5 hours at room temperature, the solution is poured onto water containing a few drops of acetic acid. The solid is filtered and crystallized from methanol to yield 6α,17α-dimethyl-4-androstene-3β,17β,19-triol.

EXAMPLE 35

17β,19-DIHYDROXY-6α,17α-DIMETHYL-4-ANDROSTEN-3-ONE

6α,17α-Dimethyl-4-androstene-3β,17β,19-triol is dissolved in hot chloroform and cooled to 15° C. Activated manganese dioxide is added at a rate such that the temperature does not rise above 25° C. Stirring is continued at room temperature for about 1 hour. The manganese dioxide is removed by filtration through diatomaceous earth and the chloroform removed by distillation under vacuum. The residue is crystallized from acetonitrile to yield 17β,19-dihydroxy-6α,17α-dimethyl-4-androsten-3-one.

EXAMPLE 36

6α,17α-DIMETHYL-4-ANDROSTENE-17β,19-DIOL

17β,19-Dihydroxy-6α,17α-dimethyl-4-androstene-3-one is dissolved in ethanedithiol. Boron trifluoride-etherate is added and after 30 minutes the reaction mixture is diluted with ether, washed with 1 N sodium hydroxide until the odor is removed and the ether solution dried over magnesium sulfate. Evaporation of the ether results in a solid which is triturated with hexane. Filtration yields the thioketal which is dissolved in methanol. Raney Nickel is added and the resulting suspension is heated at its reflux temperature for about 5 hours while being stirred. The nickel is removed by filtration and the solvent evaporated. Chromatography of the residue on silica gel, elution with benzene-ethylacetate, evaporation of the eluate and crystallization of the residue from hexane yields 6α,17α-dimethyl-4-androstene-17β,19-diol.

EXAMPLE 37

17β-HYDROXY-6α,17α-DIMETHYL-4-ANDROSTEN-19-ONE

6α,17α-Dimethyl-4-androstene-17β,19-diol is dissolved in acetone and one equivalent of Jones Reagent is added with stirring. After standing for 15 minutes the acetone layer is poured onto water. The mixture is stirred for 30 minutes, the solid which forms is removed by filtration and washed well with water. Crystallization of this material from hexane yields 17β-hydroxy-6α,17α-dimethyl-4-androsten-19-one.

EXAMPLE 38

19-ACETOXY-5α,6α-EPOXY-ANDROSTANE-3,17-DIONE BIS ETHYLENEKETAL

To a solution of 19-acetoxy-5-androstene-3,17-dione bis ethyleneketal in methylenechloride precooled to 0° C.. is added a precooled methylenechloride solution of m-chloroperbenzoic acid at 0° C. The resulting mixture is stirred at room temperature for about 24 hours and additional methylenechloride is added. The solution is washed sequentially with solutions of sodium sulfite, sodium thiosulfate, sodium bicarbonate and finally with water. The methylenechloride extract is dried over magnesium sulfate and taken to dryness under reduced pressure. Recrystallization of the residue from methanol yields 19-acetoxy-5α,6α-epoxy-androstane-3,17-dione bis ethyleneketal.

EXAMPLE 39

5α,19-DIHYDROXY-6β-METHYLANDROSTANE-3,17-DIONE BIS ETHYLENEKETAL

To a solution of 19-acetoxy-5α,6α-epoxyandrostane-3,17-dione bis ethyleneketal in tetrahydrofuran is added an ethereal solution of methylmagnesium bromide. The resultant mixture is refluxed for about 4 hours, cooled and treated with a saturated aqueous ammonium chloride solution. The organic layer is evaporated, dissolved in ethylacetate, washed with brine, dried over magnesium sulfate and concentrated. Crystallization from a solution of acetone-hexane yields 5α,19-dihydroxy-6β-methylandrostane-3,17-dione bis ethyleneketal.

EXAMPLE 40

19-HYDROXY-6α-METHYL-4-ANDROSTENE-3,17-DIONE

A solution of 5α,19-dihydroxy-6β-methylandrostane-3,17-dione bis ethyleneketal in methanol containing aqueous sulfuric acid is heated to its reflux temperature and the solvent removed. Crystallization of the residue from acetone-hexane yields 19-hydroxy-6α-methyl-4-androstene-3,17-dione.

EXAMPLE 41

6α-METHYL-4-ANDROSTENE-3,17,19-TRIONE

To a solution of 19-hydroxy-6α-methyl-4-androstene-3,17-dione in dimethylformamide at 40° C. is rapidly added one equivalent of Jones Reagent. The solution is stirred for about 5 hours at 40° C., cooled and a 1% aqueous sodium sulfite solution is added. The precipitate which forms is collected, washed well with water and crystallized from ether-hexane to yield 6α-methyl-4-androstene-3,17,19-trione.

EXAMPLE 42

4,6-ANDROSTADIENE-3,17,19-TRIONE

19-Hydroxy-4-androstene-3,17-dione and chloranil are dissolved in t-butanol which is rapidly brought to its reflux temperature. The t-butanol is removed by distillation at atmospheric pressure at such a rate that the combined reflux and distillation time equals one hour. The dark pasty residue is triturated with hot chloroform and cooled. The solid is removed by filtration and the filtrate extracted with water, a 2% sodium hydroxide solution and again with water. The organic layer is dried over magnesium sulfate and the solvent removed under vacuum to yield 19-hydroxy-4,6-androstadiene-3,17-dione. This diene so prepared is dissolved in acetone and chilled in an ice bath. Jones reagent is added over a 10 minute period and stirring continued for an additional 45 minutes. The mixture is poured onto water. The solid is filtered and recrystallized from benzene to yield 4,6-androstadiene-3,17,19-trione.

Substituting 19-hydroxy-4-methyl-4,6-androstadiene-3,17-dione for the 19-hydroxy-4,6-androstadiene-3,17-dione above results in the preparation of 4-methyl-4,6-androstadiene-3,17,19-trione.

EXAMPLE 43

7α-METHYL-4-ANDROSTENE-3β,17β,19-TRIOL

A solution of lithium dimethylcopper is prepared under nitrogen by the addition of 1.6 M ethereal methyllithium to a slurry of cuprous iodide in anhydrous ether at 0° C. The solution is stirred at 0° C. for 20 minutes and then 4,6-androstadiene-3,17,19-trione in anhydrous tetrahydrofuran is added over a 20-minute period and stirred for an additional 30 minutes. The mixture is poured onto a saturated aqueous ammonium chloride solution, benzene added and the resulting mixture is rapidly filtered through diatomaceous earth. The organic layer is washed with aqueous ammonium chloride, water, dried over magnesium sulfate and evaporated to dryness. The crude product is dissolved in aqueous methanol containing a drop of hydrochloric acid. The solution is stirred at room temperature for about one hour and then poured onto ice-water. The oil is extracted with methylenechloride, washed with water, dried over magnesium sulfate and the solvent removed. The residue is crystallized from etherhexane to yield 7α-methyl-4-androstene-3,17,19-trione.

EXAMPLE 44

17β,19-DIHYDROXY-1,4,6-ANDROSTATRIEN-3-ONE DIACETATE

17β,19-Dihydroxy-4-androsten-3-one diacetate and chloranil are dissolved in t-butanol which is rapidly brought to reflux. The t-butanol is distilled at atmospheric pressure at such a rate that the total reflux and distillation time equals one hour. The dark residue which remains is triturated with hot chloroform and filtered. The filtrate is extracted with water, a 2% sodium hydroxide solution and again with water. The organic layer is dried over magnesium sulfate and the solvent removed to yield 17β,19-dihydroxy-4,6-androstadien-3-one diacetate. The diene so prepared is refluxed with dichlorodicyanobenzoquinone in anhydrous dioxane for a period of about 48 hours. The mixture is cooled, filtered and the filtrate poured onto a mixture of methylenechloride and water. The organic layer is separated, washed with water, dried well over magnesium sulfate and the solvent removed. The dark residue remaining is chromatographed on silica gel and eluted with methylenechloride to yield from the eluate the desired 17β,19-dihydroxy-1,4,6-androstatrien-3-one diacetate.

EXAMPLE 45

17β,19-DIHYDROXY-1α-METHYL-4,6-ANDROSTADIEN-3-ONE DIACETATE

A solution of lighium dimethylcopper is lithium under nitrogen by the addition of 1.6 M ethereal methyllithium to an ether slurry of curpous iodide at 0° C. The solution is stirred at 0° C. for 20 minutes and a solution of 17β,19-dihydroxy-1,4,6-androstatrien-3-one diacetate in anhydrous tetrahydrofuran is added over a 20-minute period and stirred for an additional 30 minutes. The mixture is poured onto a saturated aqueous ammonium chloride solution, benzene is added and the resulting mixture filtered through diatomaceous earth. The organic layer is washed with aqueous ammonium chloride, water, dried over magnesium sulfate and evaporated to dryness. The residue is crystallized from hexane to give 17β,19-dihydroxy-1α-methyl-4,6-androstadien-3-one diacetate.

EXAMPLE 46

17β,19-DIHYDROXY-1α,7α-DIMETHYL-4-ANDROSTEN-3-ONE DIACETATE

A solution of 17β,19-dihydroxy-1α-methyl-4,6-androstadien-3-one diacetate in anhydrous tetrahydrofuran is added slowly to an ice cold ethereal solution of lithium dimethylcopper prepared as in the preceding Example. Stirring is continued for 30 minutes and the mixture is poured onto a saturated aqueous ammonium chloride solution. Benzene is added and the mixture filtered through diatomaceous earth. The organic layer is washed with aqueous ammonium chloride, water, dried over magnesium sulfate and evaporated to dryness. The residue is stirred at room temperature with aqueous methanolic hydrochloric acid for 1 hour and poured onto ice water. The gum which forms is extracted with ether, washed with water, dried over magnesium sulfate and the ether removed. The residue is chromatographed on silica gel and eluted with benzene. The eluate is recrystallized from hexane to give 17β,19-dihydroxy-1α,7α-dimethyl-4-androsten-3-one diacetate.

EXAMPLE 47

17β,19-DIHYDROXY-1α,7α-DIMETHYL-4-ANDROSTEN-3-ONE

17β,19-Dihydroxy-1α,7α-dimethyl-4-androsten-3-one diacetate is dissolved under nitrogen in a sodium methoxide methanol solution at 0° C. and stirred at room temperature for 2 hours. The solution is poured onto water and the solid collected by filtration. Recrystallization from acetonitrile yields the desired 17β,19-dihydroxy-1α,7α-dimethyl-4-androsten-3-one.

EXAMPLE 48

1α,7α-DIMETHYL-4-ANDROSTENE-3,17,19-TRIONE

To a solution of 17β, 19-dihydroxy-1α,7α-dimethyl-4-androsten-3-one in acetone at 20° C. is added two equivalents of Jones Reagent and the mixture stirred for 30 minutes. The acetone layer is poured onto water with vigorous stirring. The crystals are removed by suction filtration and air dried. Crystallization from an acetone-hexane solution yields 1α,7α-dimethyl-4-androstene-3,17,19-trione.

EXAMPLE 49

17β,19-DIHYDROXY-1α,7α-DIMETHYL-4-ANDROSTEN-3-ONE 17-ACETATE

To a solution of 17β,19-dihydroxy-1α,7α-dimethyl-4-androsten-3-one diacetate in 10% aqueous methanol is added 1 equivalent of sodium bicarbonate. The resulting solution is heated at reflux temperature for one hour. Methanol is removed under vacuum to half volume and the concentrate is poured onto water. The solid which forms is filtered, air dried and crystallized from hexane to give 17β,19-dihydroxy-1α,7α-dimethyl-4-androsten-3-one 17-acetate.

EXAMPLE 50

17β-HYDROXY-1α,7α-DIMETHYL-4-ANDROSTENE-3,19-DIONE ACETATE

One equivalent of Jones Reagent is added to a well stirred solution of 17β,19-dihydroxy-1α,7α-dimethyl-4-androsten-3-one 17-acetate in acetone at 20° C. After 30 minutes the upper acetone layer is poured into water with vigorous stirring. After one hour, the solid is collected by suction filtration, washed with water and air dried. Crystallization of the solid from an ether-hexane solution yields 17β-hydroxy-1α,7α-dimethyl-4-androstene-3,19-dione acetate.

EXAMPLE 51

19-HYDROXY-4-METHYL-4-ANDROSTENE-3,17-DIONE

A mixture of 19-hydroxy-4-androstene-3,17-dione, thiophenol, 40% aqueous formaldehyde, triethylamine and ethanol are heated at the reflux temperature for about 48 hours. The cooled solution is poured into an aqueous sodium hydroxide solution and the product isolated by ether extraction. The ether extract is washed with water, dried over magnesium sulfate and the solvent removed under reduced pressure. The residue is triturated with hot hexane to remove the condensation products derived from the thiophenol and formaldehyde. The 19-hydroxy-4-phenylthiomethyl-4-androsten-3,17-dione so obtained is desulfurized by dissolving in acetone and adding to a suspension of Raney Nickel in refluxing acetone. The mixture is heated at its reflux temperature while stirring for about 5 hours. The hot solution is filtered and the nickel washed with boiling ethanol and water. The combined filtrates are concentrated under vacuum whereupon the product separates as a solid. Recrystallization from an acetone-hexane solution yields 19-hydroxy-4-methyl-4-androstene-3,17-dione.

Substituting 19-hydroxy-7α-methyl-4-androstene-3,17-dione and 19-hydroxy-1α-methyl-4-androstene-3,17-dione for the 19-hydroxy-4-androstene-3,17-dione above results in the preparation of 19-hydroxy-4,7α-dimethyl-4-androstene-3,17-dione and 19-hydroxy-1α,4-dimethyl-4-androstene-3,17-dione.

EXAMPLE 52

19-HYDROXY-4-METHYL-4-ANDROSTENE-3,17-DIONE ACETATE

19-Hydroxy-4-methyl-4-androstene-3,17-dione is stirred under nitrogen with acetic anhydride and pyridine for about 16 hours. The yellow solution is poured onto water and the precipitate collected by suction filtration and washed well with water. Crystallization from acetone-hexane yields the desired 19-hydroxy-4-methyl-4-androstene-3,17-dione acetate.

Substituting 19-hydroxy-1α-methyl-4-androstene-3,17-dione, 19-hydroxy-1β-methyl-4-androstene-3,17-dione, 19-hydroxy-6α-methyl-4-androstene-3,17-dione, 19-hydroxy-1α,7α-dimethyl-4-androstene-3,17-dione, 19-hydroxy-7α-methyl-4-androstene-3,17-dione, 19-hydroxy-4,7α-dimethyl-4-androstene-3,17-dione and 19-hydroxy-1α,4-dimethyl-4-androstene-3,17-dione for the 19-hydroxy-4-methyl-4-androstene-3,17-dione above results in the preparation of 19-hydroxy-1α-methyl-4-androstene-3,17-dione acetate, 19-hydroxy-1β-methyl-4-androstene-3,17-dione acetate, 19-hydroxy-6α-methyl-4-androstene-3,17-dione acetate, 19-hydroxy-1α,7α-dimethyl-4-androstene-3,17-dione acetate, 19-hydroxy-7α-methyl-4-androstene-3,17-dione acetate, 19-hydroxy-4,7α-dimethyl-4-androstene-3,17-dione acetate and 19-hydroxy-1α,4-dimethyl-4-androstene-3,17-dione acetate, respectively.

EXAMPLE 53

17β,19-DIHYDROXY-4-METHYL-4-ANDROSTEN-3-ONE 19-ACETATE

To a solution of 19-hydroxy-4-androstene-3,17-dione acetate in ethanol chilled to 5° C. is added potassium borohydride. The reaction mixture is stirred under nitrogen at 5° C. At the end of the 5 hour reaction time, the solution is poured onto water and acidified with glacial acetic acid. The precipitate which forms is filtered, washed well with water and dried in a vacuum oven at 60° C. After crystallization from acetone-hexane, the compound 17β,19-dihydroxy-4-methyl-4-androsten-3-one 19-acetate is obtained.

Substituting 19-hydroxy-1α-methyl-4-androstene-3,17-dione acetate, 19-hydroxy-1β-methyl-4-androstene-3,17-dione acetate, 19-hydroxy-6α-methyl-4-androstene 3,17-dione acetate, 19-hydroxy-1α,7α-dimethyl-4-androstene-3,17-dione acetate, 19-hydroxy-7αmethyl-4-androstene-3,17-dione acetate, 19-hydroxy-4,7α-dimethyl-4-androstene-3,17-dione acetate and 19-hydroxy-1α,4-dimethyl-4-androsten-3,17-dione acetate for the 19-hydroxy-4-methyl-4-androstene-3,17-dione above results in the preparation of 17β,19-dihydroxy-1α-methyl-4-androstene-3-one 19-acetate, 17β,19-dihydroxy-1β-methyl-4-androstene-3-one 19-acetate, 17β,19-dihydroxy-6α-methyl-4-androsten-3-one 19-acetate, 17β,19-dihydroxy-1α,7α-dimethyl-4-androsten-3-one 19-acetate, 17β,19-dihydroxy-7α-methyl-4-androstene-3-one 19-acetate, 17β,19-dihydroxy-4,7α-dimethyl-4-androsten-3-one 19-acetate and 17β,19-dihydroxy-4,7α-dimethyl-4-androsten-3-one 19-acetate, respectively.

EXAMPLE 54

19-HYDROXY-4-METHYL-17β-(2'-TETRAHYDROPYRANLOXY)-4-ANDROSTEN-3-ONE ACETATE

To a stirred solution of 17β,19-dihydroxy-4-methyl-4-androsten-3-one 19-acetate and p-toluenesulfonic acid in anhydrous dioxane is added dihydropyran slowly. After 5 minutes, methanolic ammonia is added until the solution is slightly basic and the solvent removed under vacuum. The residual oil is dissolved in methylenechloride and the solution extracted with aqueous sodium bicarbonate, dried over sodium sulfate and concentrated under vacuum. The residue is crystallized from hexane to yield 19-hydroxy-4-methyl-17β-(2'-tetrahydropyranyloxy)-4-androsten-3-one acetate.

Substituting 17β,19-dihydroxy-1α-methyl-4-androsten-3-one 19-acetate, 17β,19-dihydroxy-1β-methyl-4-androsten-3-one 19-acetate, 17β,19-dihydroxy-6α-methyl-4-androsten-3-one 19-acetate, 17β,19-dihydroxy-1α,7α-dimethyl-4-androsten-3-one 19-acetate, 17β,19-dihydroxy-7α-methyl-4-androsten-3-one 19-acetate, 17β,19-dihydroxy-4,7α-dimethyl-4-androsten-3-one 19-acetate and 17β,19-dihydroxy-1α,4-dimethyl-4-androsten-3-one 19-acetate for the 17β,19-dihydroxy-4-methyl-4-androsten-3-one 19-acetate above results in the preparation of 19-hydroxy-1α-methyl-17β-(2'-tetrahydropyranyloxy)-4-androsten-3-one acetate, 19-hydroxy-1β-methyl-17β-(2'-tetrahydropyranyloxy)-4-androsten-3-one acetate, 19-hydroxy-6α-methyl-17β-(2'-tetrahydropyranyloxy)-4-androsten-3-one acetate, 19-hydroxy-1α,7α-dimethyl-17β-(2'-tetrahydropyranyloxy)-4-androsten-3-one acetate, 19-hydroxy-7α-methyl-17β-(2'-tetrahydropyranyloxy)-4-androsten-3-one acetate, 19-hydroxy-4,7α-dimethyl-17β-(2'-tetrahydropyranyloxy)-4-androsten-3-one acetate and 19-hydroxy-1α,4-dimethyl-17β-(2'-tetrahydropyranyloxy)-4-androsten-3-one acetate, respectively.

EXAMPLE 55

19-HYDROXY-4-METHYL-17β-(2'-TETRAHYDROPYRANYLOXY)-4-ANDROSTEN-3-ONE

A solution of 19-hydroxy-4methyl-17β-(2'-tetrahydropyranyloxy)-4-androsten-3-one acetate and sodium bicarbonate in 10% aqueous methanol is refluxed for one hour, concentrated to half volume and poured onto water with stirring. The oil which forms is extracted into ether. The ether extract is washed with water, dried over magnesium sulfate and the ether evaporated. The residue is crystallized from hexane to yield 19-hydroxy-4-methyl-17β-(2'-tetrahydropyranyloxy)-4-androsten-3-one.

Substituting 19-hydroxy-1α-methyl-17β-(2'-tetrahydropyranyloxy)-4-androsten-3-one acetate, 19-hydroxy-1β-methyl-17β-(2'-tetrahydropyranyloxy)-4- androsten-3-one acetate, 19-hydroxy-6α-methyl-17β-(2'-tetrahydropyranyloxy)-4-androsten-3-one acetate, 19-hydroxy-1α,7α-dimethyl-17β-(2'-tetrahydropyranyloxy)-4-androsten-3-one acetate, 19-hydroxy-4,7α-dimethyl-17β-(2'-tetrahydropyranyloxy)-4-androsten-3-one acetate, 19-hydroxy-7α-methyl-17β-(2'-tetrahydropyranyloxy)-4-androsten-3-one acetate and 19-hydroxy-1α,4-dimethyl-17β-(2'-tetrahydropyranyloxy)-4-androsten-3-one acetate for the 19-hydroxy-4-methyl-17β-(2'-tetrahydropyranyloxy)-4-androsten-3-one acetate above results in the preparation of 19-hydroxy-1α-methyl-17β-(2'-tetrahydropyranyloxy)-4-androsten-3-one, 19-hydroxy-1β-methyl-17β-(2'-tetrahydropyranyloxy)-4-androsten-3-one, 19-hydroxy-6α-methyl-17β-(2'-tetrahydropyranyloxy)-4-androsten-3-one, 19-hydroxy-1α,7α-dimethyl-17β-(2'-tetrahydropyranyloxy)-4-androsten-3-one, 19-hydroxy-4,7α-dimethyl-17β-(2'-tetrahydropyranyloxy)-4-androsten-3-one, 19-hydroxy-7α-methyl-17β-(2'-tetrahydropyranyloxy)-4-androsten-3-one and 19-hydroxy-1α,4-dimethyl-17β-(2'-tetrahydropyranyloxy)-4-androsten-3-one, respectively.

EXAMPLE 56

4-METHYL-17β-(2'-TETRAHYDROPYRANYLOXY)-4-ANDROSTENE-3,19-DIONE

To a solution of 19-hydroxy-4-methyl-17β-(2'-tetrahydropyranyloxy)-4-androsten-3-one in acetone chilled to 10° C. is added exactly one equivalent of Jones Reagent. After 30 minutes the upper acetone layer is poured onto water with vigorous stirring. The solid is filtered under suction, air dried and crystallized from hexane to yield 4-methyl-17β-(2'-tetrahydropyranyloxy)-4-androsten-3,19-dione.

Substituting 19-hydroxy-1α-methyl-17β-(2'-tetrahydropyranyloxy)-4-androsten-3-one, 19-hydroxy-1β-methyl-17β-(2'-tetrahydropyranyloxy)-4-androsten-3-one, 19-hydroxy-6α-methyl-17β-(2'-tetrahydropyranyloxy)-4-androsten-3-one, 19-hydroxy-1α-dimethyl-17β-(2'-tetrahydropyranyloxy)-4-androsten-3-one, 19-hydroxy-4,7α-dimethyl-17β-(2'-tetrahydropyranyloxy)-4-androsten-3-one, 19-hydroxy-7α-methyl-17β-(2'-tetrahydropyranyloxy)-4-androsten-3-one and 19-hydroxy-1α,4-dimethyl-4-dimethyl-17β-(2'-tetrahydropyranyloxy)-4-androsten-3-one for the 19-hydroxy-4-methyl-17β-(2'-tetrahydropyranyloxy)-4-androsten3-one above results in the preparation of 1α-methyl-17β-(2'-tetrahydropyranyloxy)-4-androstene-3,19-dione, 1β-methyl-17β-(2'-tetrahydropyranyloxy)-4-androstene-3,19-dione, 6α-methyl-17β-(2'-tetrahydropyranyloxy)-4-androstene-3,19-dione, 1α,7α-dimethyl-17β-(2'-tetrahydropyranyloxy)-4-androstene-3,19-dione, 4,7α-dimethyl-17β-(2'-tetrahydropyranyloxy)-4-androstene-3,19-dione, 7α-methyl-17β-(2'-tetrahydropyranyloxy)-4-androstene-3,19-dione and 1α,4-dimethyl-17β-(2'-tetrahydropyranyloxy)-4-androsten-3,19-dione, respectively.

EXAMPLE 57

19-HYDROXY-4-METHYL-17β-(TETRAHYDROPYRAN-4'-YLOXY)-ANDROST-4-EN-3-ONE

17β,19-Dihydroxy-4-methyl-4-androsten-3-one 19-acetate is dissolved in dimethylformamide and heated to 50° C. 4-Bromotetrahydropyran is added followed by sodium hydride. Heating and stirring is continued for about 4 hours and the cooled reaction mixture is poured onto ice water. The oil which forms is extracted with ether and the ether extracts are washed with water, dried over magnesium sulfate and concentrated to leave a solid. Crystallization of this solid from hexane yields 19-hydroxy-4-methyl-17β-(tetrahydropyran-4'-yloxy)-androst-4-en-3-one acetate which is refluxed for a period of about one hour in a 10% aqueous methanol solution containing sodium bicarbonate. The methanol is removed to half volume and the concentrate is poured onto water. The ether extract is washed with water, dried over magnesium sulfate and concentrated in vacuo. Crystallization of the residue from hexane yields 19-hydroxy-4-methyl-17β-(tetrahydropyran-4'-yloxy)androst-4-en-3-one.

Substituting 17β,19-dihydroxy-1α-methyl-4-androsten-3-one 19-acetate, 17β,19-dihydroxy-1β-methyl-4-androsten-3-one 19-acetate, 17β,19-dihydroxy-6α-methyl-4-androsten-3-one 19-acetate, 17β,19-dihydroxy-1α,7α-dimethyl-4-androsten-3-one 19-acetate, 17β,19-dihydroxy-7α-methyl-4-androsten-3-one 19-acetate, 17β,19-dihydroxy-4,7α-dimethyl-4-androsten-3-one 19-acetate and 17β,19-dihydroxy-1α,4-dimethyl-4-androsten-3-one 19-acetate for the 17β,19-dihydroxy- 4-methyl-4-androsten-3-one 19-acetate above results in the preparation of 19-hydroxy-1α-methyl-17β-(tetrahydropyran-4'-yloxy)androst-4-en-3-one, 19-hydroxy-1β-methyl-17β-(tetrahydropyran-4'-yloxy)androst-4-en-3-one, 19-hydroxy-6α-methyl-17β-(tetrahydropyran-4'-yloxy)androst-4-en-3-one, 19-hydroxy-1α,7α-dimethyl-17β-(tetrahydropyran-4'-yloxy)androst-4-en-3-one, 19-hydroxy-7α-methyl-17β-(tetrahydropyran-4'-yloxy)androst-4-en-3-one, 19-hydroxy-4,7α-dimethyl-17β-(tetrahydropyran-4'-yloxy)-androst-4-en-3-one and 19-hydroxy-1α,4-dimethyl-17β-(tetrahydropyran-4'-yloxy)androst-4-en-3-one, respectively.

EXAMPLE 58

4-METHYL-17β-(TETRAHYDROPYRAN-4'-YLOXY)-4-ANDROSTENE-3,19-DIONE

To a solution of 19-hydroxy-4-methyl-17β-(tetrahydropyran-4'-yloxy)-androst-4-en-3-one in acetone chilled to 10° C. is added one equivalent of Jones Reagent. After 30 minutes the acetone layer is decanted and poured onto water with vigorous stirring. The solid is filtered, dried in a vacuum over and crystallized from hexane to yield 4-methyl-17β-(tetrahydropyran-4'-4-androstene-3,19-dione.

Substituting 19-hydroxy-1α-methyl-17β-(tetrahydropyran-4'-yloxy)-androst-4-en-3-one, 19-hydroxy-1β-methyl-17β-(tetrahydropyran-4'-yloxy)androst-4-en-3-one, 19-hydroxy-6α-methyl-17β-(tetrahydropyran-4'-yloxy)androst-4-en-3-one, 19-hydroxy-1α,7α-dimethyl-17β-(tetrahydropyran-4'-yloxy)androst-4-en-3-one, 19-hydroxy-7α-methyl-17β-(tetrahydropyran-4'-yloxy)androst-4-en-3-one, 19-hydroxy- 4,7α-dimethyl-17β-(tetrahydropyran-4'-yloxy)androst-4-en-3-one and 19-hydroxy-1α,4-dimethyl-17β-(tetrahydropyran-4'-yloxy)androst-4-en-3-one for the 19-hydroxy-4-methyl-17β-(tetrahydropyran-4'-yloxy)androst-4-en-3-one above results in the preparation of 1α-methyl-17β-(tetrahydropyran-4'-yloxy)androst-4-en-3,19-dione, 1β-methyl-17β-(tetrahydropyran-4'-yloxy)androst-4-ene-3,19-dione, 6α-methyl-17β-(tetrahydropyran-4'-yloxy)androst-4-ene-3,19-dione, 1α7α-dimethyl-17β-(tetrahydropyran-4'-yloxy)androst-4-ene-3,19-dione, 7α-methyl-17β-(tetrahydropyran-4'-yloxy)androst-4-ene-3,19-dione, 4,7α-dimethyl-17β-(tetrahydropyran-4'-yloxy)androst-4-ene-3,19-dione and 1α4-dimethyl-17β-(tetrahydropyran-4'-yloxy)androst-4-ene-3,19-dione, respectively.

EXAMPLE 59

19-HYDROXY-4-METHYL-17β-TRIPHENYL-SILOXY-ANDROST-4-EN-3-ONE

17β,19-Dihydroxy-4-methyl-4-androsten-3-one 19-acetate, triphenylsilylchloride and pyridine are mixed in dry dimethylformamide and heated on a steam bath overnight. The reaction mixture is poured onto water and stirred well for 15 minutes. The solid is filtered and air dried. Crystallization from hexane yields 19-hydroxy-4-methyl-17β-triphenylsiloxy-4-androstene-3-one acetate, which is refluxed for one hour in 10% aqueous methanol containing sodium bicarbonate. The methanol is removed to half volume and the concentrate is poured onto water. The ether extract is washed with water, dried over magnesium sulfate and concentrated in vacuo. The residue is crystallized from hexane to yield 19-hydroxy-4-methyl-17β-triphenylsiloxy-androst-4-en-3-one.

Substituting 17β,19-dihydroxy-1α-methyl-4-androsten-3-one 19-acetate, 17β,19-dihydroxy-1β-methyl-4-androsten-3-one 19-acetate, 17β,19-dihydroxy-6α-methyl-4-androsten-3-one 19-acetate, 17β,19-dihydroxy-1α,7α-dimethyl-4-androsten-3-one 19-acetate, 17β,19-dihydroxy-7α-methyl-4-androsten-3-one 19-acetate, 17β,19-dihydroxy-4,7α-dimethyl-4-androsten-3-one 19-acetate and 17β,19-dihydroxy-1α,4-dimethyl-4-androsten-3-one 19-acetate for the 17β,19-dihydroxy-4-methyl-4-androsten-3-one 19-acetate above, results in the preparation of 19-hydroxy-1α-methyl-17β-triphenylsiloxy-4-androsten-3-one, 19-hydroxy-1β-methyl-17β-triphenylsiloxy-4-androsten-3-one, 19-hydroxy-6α-methyl-17β-triphenylsiloxy-4-androsten-3-one, 19-hydroxy-1α,7α-dimethyl-17β-triphenylsiloxy-4-androsten-3-one, 19-hydroxy-7α-methyl-17β-triphenylsiloxy-4-androsten-3-one and 19-hydroxy-1α,4-dimethyl-17β-triphenylsiloxy-4-androsten-3-one, respectively.

EXAMPLE 60

4-METHYL-17β-TRIPHENYLSILOXY-4-ANDROSTENE-3,19-DIONE

To a solution of 19-hydroxy-4-methyl-17β-triphenylsiloxy-androst-4-en-3-one in acetone chilled to 10° C. is added one equivalent of Jones Reagent. After 30 minutes, the acetone layer is decanted and poured onto water with vigorous stirring. The solid is filtered, dried in a vacuum oven and crystallized from hexane to yield 4-methyl-17β-triphenylsiloxy-4-androstene-3,19-dione.

Substituting 19-hydroxy-1α-methyl-17β-triphenylsiloxy-4-androsten-3-one, 19-hydroxy-1β-methyl-17β-triphenylsiloxy-4-androsten-3-one, 19-hydroxy-6α-methyl-17β-triphenylsiloxy-4-androsten-3-one, 19-hydroxy-1α,7α-dimethyl-17β-triphenylsiloxy-4-androsten-3-one, 19-hydroxy-7α-methyl-17β-triphenylsiloxy-4-androsten-3-one, 19-hydroxy-4,7α-dimethyl-17β-triphenylsiloxy-4-androsten-3-one, and 19-hydroxy-1α,4-dimethyl-17β-triphenylsiloxy-4-androsten-3-one for the 19-hydroxy-4-methyl-17β-triphenylsiloxy-androst-4-en-3-one above results in the preparation of 1α-methyl-17β-triphenylsiloxy-4-androstene-3,19-dione, 1β-methyl-17β-triphenylsiloxy-4-androstene-3,19-dione, 6α-methyl-17β-triphenylsiloxy-4-androstene-3,19-dione, 1α,7α-dimethyl-17β-triphenylsiloxy-4-androstene-3,19-dione, 7αmethyl-17α-triphenylsiloxy-4-androstene-3,19-dione, 4,7α-dimethyl-17β-triphenylsiloxy-4-androstene-3,19-dione and 1α,4-dimethyl-17β-triphenylsiloxy-4-androstene-3,19-dione, respectively.

EXAMPLE 61

ANDROST-4-ENE-3β,17β,19-TRIOL 17,19-DIACETATE

To a solution of lithium tri-t-butoxyaluminum hydride in tetrahydrofuran is added a tetrahydrofuran solution of 17β,19-dihydroxy-4-androsten-3-one diacetate. The resulting mixture is stirred at 20° C. for a period of about 18 hours after which an aqueous solution of sodium potassium tartrate is added. The mixture is filtered and concentrated to a small volume under reduced pressure. The concentrate is taken up in ether and washed well with water. The ether solution is dried over magnesium sulfate, filtered and the ether removed under vacuum to yield a residue which is crystallized from acetone-hexane to yield androst-4-ene-3β,19-triol 17,19-diacetate.

Substituting 17β,19-dihydroxy-1α,7α-dimethyl-4-androsten-3-one diacetate, 17β,19-dihydroxy-6α,17α-dimethyl-4-androsten-3-one diacetate, 17β,19-dihydroxy-4,17α-dimethyl-4-androsten-3-one diacetate, 17α,19-dihydroxy-1β-methyl-4-androsten-3-one diacetate, 17β,19-dihydroxy-4,7α-dimethyl-4-androsten-3-one diacetate, 17β,19-dihydroxy-7,17α-dimethyl-4-androsten-3-one diacetate, 17β,19-dihydroxy-17α-vinyl-4-androsten-3-one diacetate, 17β,19-dihydroxy-17α-methyl-4-androsten-3-one diacetate and 17α-ethinyl-17β,19-dihydroxy-4-androsten-3-one diacetate for the 17β,19-dihydroxy-4-androsten-3-one diacetate above results in the preparation of 1α,7α-dimethyl-4-androstene-3β, 17β,19-triol 17,19-diacetate, 6α,17α-dimethyl-4-androstene-3β,17β,19-triol 17,19-diacetate, 4,17α-dimethyl-4-androstene-3β,17β,19-triol 17,19-diacetate, 1α-methyl-4-androstene-3β,17β,19-triol 17,19-diacetate, 4,7α-dimethyl-4-androstene-3β,17β,19-triol 17,19-diacetate, 7,17α-dimethyl-4-androstene-3β,17β,19-triol 17,19-diacetate, 17α-vinyl-4-androstene-3β,17β,19-triol 17,19-diacetate, 17α-methyl-4-androstene-3β,17β,19-triol 17,19-diacetate and 17α-ethinyl-4-androstene-3β,17β,19-triol 17,19-diacetate, respectively.

EXAMPLE 62

3β(2'-TETRAHYDROPYRANYLOXY)-ANDROST-4-ENE-17β, 19-DIOL 17-ACETATE

A solution of androst-4-ene-3β,17β,19-triol 17,19-diacetate, p-toluenesulfonic acid and 2,3-dihydropyran are stirred for three hours at room temperature. The reaction solution is diluted with ether, washed with an aqueous sodium carbonate solution, washed with water, dried over sodium sulfate and evaporated to dryness under reduced pressure. Crystallization of the residue from acetone-hexane yields 3β-(2'-tetrahydropyranyloxy)-4-androstene-17β,19-diol diacetate. This product is then refluxed for one hour in 10% aqueous methanol containing 1 equivalent of sodium bicarbonate. The solution is concentrated to half volume under reduced pressure and diluted with water. The crystals are removed by suction filtration, washed with water and air dried. Crystallization from an acetone-hexane solution yields 3β-(2'-tetrahydropyranyloxy)-androst-4-ene-17β,19-diol 17-acetate.

Substituting 1α,7α-dimethyl-4-androstene-3α,1-7α,19-triol 17,19-diacetate, 6α,17α-dimethyl 4-androstene-3β,17β,19-triol 17,19-diacetate, 4,17α-dimethyl-4-androstene-3β,17β,19-triol 17,19-diacetate and 1α-methyl-4-androstene-3β,17β,19-triol 17,19-diacetate for the androst-4-ene-3β,17β,19-triol 17,19-diacetate above results in the preparation of 1α,7α-dimethyl-3β-(2'-tetrahydropyranyloxy)-4-androstene-17β,19-diol 17-acetate, 6α,17α-dimethyl-3β-(2'-tetrahydropyranyloxy)-4-androstene-17β,19-diol 17-acetate, 4,17α-dimethyl-3β-(2'-tetrahydropyranyloxy)-4-androstene-17β,19-diol 17-acetate and 1α-methyl-3β-(2'-tetrahydropyranyloxy)-4-androstene-17β,19-diol 17-acetate, respectively.

EXAMPLE 63

17β-HYDROXY-3β-(2'-TETRAHYDROPYRANYLOXY)-4-ANDROSTEN-19-ONE ACETATE

One equivalent of Jones Reagent is added to a solution of 3β-(2'-tetrahydropyranyloxy)-4-androsten-17β,19-diol 17-acetate in acetone at 10° C. After stirring for 15 minutes the acetone layer is poured into cold water with vigorous stirring. The solid is filtered, washed with water and dried in a vacuum oven. Crystallization from hexane yields the desired 17β-hydroxy-3β-(2'-tetrahydropyranyloxy)-4-androsten-19-one acetate.

Substituting 1α,7α-dimethyl-3β-(2'-tetrahydropyranyloxy)-4-androstene-17β,19-diol 17-acetate, 6α,17α-dimethyl-3β-(2'-tetrahydropyranyloxy)-4-androstene-17β,19-diol 17-acetate, 4,17α-dimethyl-3β-(2'-tetrahydropyranyloxy)-4-androstene-17β,19-diol 17-acetate and 1α-methyl-3β-(2'-tetrahydropyranyloxy)-4-androstene-17β,19-diol 17-acetate for the 3β-(2'-tetrahydropyranyloxy)-4-androstene-17β,19-diol 17-acetate above results in the preparation of 17β-hydroxy-1α,7α-dimethyl-3β-(2'-tetrahydropyranyloxy)-4-androsten-19-one acetate, 17β-hydroxy-6α,17α-dimethyl-3β-(2'-tetrahydropyranyloxy)-4-androsten-19-one acetate, 17β-hydroxy-4,17α-dimethyl-3β-(2'-tetrahydropyranyloxy)-4-androsten-19-one acetate and 17β-hydroxy-1α-methyl-3β(2'-tetrahydropyranyloxy)-4-androstene-19-one acetate, respectively.

EXAMPLE 64

3β-(1'-METHOXY-1'-CYCLOPENTYLOXY)-4-ANDROSTENE8-17β,19-DIOL 17-ACETATE

To a solution of 4-androstene-3β,17β,19-triol 17,19-diacetate in dioxane is added with stirring cyclopentanone methylenol ether and pyridine p-toluenesulfonate. A precipitate quickly forms. After standing overnight, it is filtered and crystallized from methanol to yield 3β-(1'-methoxy-1'-cyclopentyloxy)-4-androstene-17β,19-diol 17,19-diacetate. This product is refluxed for one hour in 10% aqueous methanol containing 1 equivalent of sodium bicarbonate. The cooled solution is poured onto ice water. The crystals are filtered, washed with water and air dried. Crystallization from methanol yields 3β-(1'-methoxy-1'-cyclopentyloxy)-4-androstene-17β,19-diol 17-acetate.

Substituting 4,7α-dimethyl-4-androstene-3β,17β,19-triol 17,19-diacetate, 7α,17α-dimethyl-4-androstene-3β,17β,19-triol 17,19-diacetate and 17α-vinyl-4-androstene-3β,17β,19-triol 17,19-diacetate for the 4-androstene-3β,17β,19-triol 17,19-diacetate above results in the preparation of 3β-(1'-methoxy-1'-cyclopentyloxy)-4,7α-dimethyl-4-androstene-17β,19-diol 17-acetate, 3β-(1'-methoxy-1'-cyclopentyloxy)-7α,17α-dimethyl-4-androstene-17β,19-diol 17-acetate and 3β-(1'-methoxy-1'-cyclopentyloxy)-17α-vinyl-4-androstene-17β,19-diol 17-acetate, respectively.

EXAMPLE 65

17β-HYDROXY-3β-(1'-METHOXY-1'-CYCLOPENTYLOXY-4-ANDROSTENE-19-ONE ACETATE

One equivalent of Jones Reagent is added to a solution of 3β-(1'-cyclopentyloxy)-4-androstene-17β,19-diol 17-acetate in acetone at 10° C. After stirring for 30 minutes the acetone layer is poured onto cold water with vigorous stirring. The precipitate is filtered, washed with water and air dried. Crystallization from ether-hexane yields 17β-hydroxy-3β-(1'-methoxy-1'-cyclopentyloxy)-4-androsten-19-one acetate.

Substituting 3β-(1'-methoxy-1'-cyclopentyloxy)-4,7α-dimethyl-4-androstene-17β,19-diol 17-acetate, 3β-(1'-methoxy-1'-cyclopentyloxy)-7α,17α-dimthyl-4-androstene-17β,19-diol 17-acetate and 3β-(1'-methoxy-1'-cyclopentyloxy)-17α-vinyl-4-androstene-17β,19-diol 17-acetate for the 3β-(1'-methoxy-1'-cyclopentyloxy)-4-androstene-17β,19-diol 17-acetate above results in the preparation of 17β-hydroxy-3β-(1'-methoxy-1'-cyclopentyloxy)-4,7α-dimethyl-4-androsten-19-one acetate, 17β-hydroxy-3β-(1'-methoxy-1'-cyclopentyloxy)-7α,17α-dimethyl-4-androsten-19-one acetate and 17β-hydroxy-3β-(1'-methoxy-1'-cyclopentyloxy)-17α-vinyl-4-androsten-19-one acetate, respectively.

EXAMPLE 66

3β-(1'-CYCLOPENTENYLOXY)-4-ANDROSTENE-17β,19-DIOL 17-ACETATE

3β-(1'-Methoxy-1'-cyclopentyloxy)-4-androstene-17β,19-diol 17-acetate is dissolved in anhydrous dimethylformamide containing a drop of pyridine. The solution is heated to its reflux temperature and the alcohol distilled as it forms. After one hour, the remaining solvent is distilled under vacuum and the residue crystallized from methanol to yield 3β-(1'-cyclopentenyloxy)-4-androstene-17β,19-diol 17-acetate.

Substituting 3β-(1'-methoxy-1'-cyclopentyloxy)-4,7α-dimethyl-4-androstene-17β,19-diol 17-acetate, 3β-(1'-methoxy-1'-cyclopentyloxy)-7α,17α-dimethyl-4-androstene-17β,19-diol 17-acetate and 3β-(1'-methoxy-1'-cyclopentyloxy)-17α-vinyl-4-androsten-17β,19-diol 17-acetate for the 3β-(1'-methoxy-1'-cyclopentyloxy)-4-androstene-17β,19-diol 17-acetate above results in the preparation of 3β-(1'-cyclopentenyloxy)-4,7α-dimethyl-4-androstene-17β,19-diol 17-acetate, 3β-(1'-cyclopentenyloxy)-7α,17α-dimethyl-4-androstene-17β,19-diol 17-acetate and 3β-(1'-cyclopentenyloxy)-17α-vinyl-4-androstene-17β,19-diol 17-acetate, respectively.

EXAMPLE 67

3β-(1'-CYCLOPENTENYLOXY)-17β-HYDROXY-4-ANDROSTENE-19-ONE ACETATE

To a solution of 3β-(1'-cyclopentenyloxy)-4-androstene-17β,19-diol 17-acetate in acetone chilled to 10° C. is added one equivalent of Jones Reagent. After stirring for 30 minutes the acetone layer is poured onto water. The precipitate is filtered under vacuum, washed with water, air dried and crystallized from an ether-hexane solution to yield 3β-(1'-cyclopentenyloxy)-17β-hydroxy-4-androsten-19-one acetate.

Substituting 3β-(1'-cyclopentenyloxy)-4,7α-dimethyl-4-androstene-17β,19-diol 17-acetate, 3β-(1'-cyclopentenyl-oxy)-7α,17α-dimethyl-4-androstene-17β,19-diol 17-acetate and 3β-(1'-cyclopentenyloxy)-17α-vinyl-4-androstene-17β,19-diol 17-acetate for the 3β-(1'-cyclopentenyloxy)-4-androstene-17β,19-diol 17-acetate above results in the preparation of 3β-(1'-cyclopentenyloxy)-17β-hydroxy-4,7α-dimethyl-4-androsten-19-one acetate, 3β-(1'-cyclopentenyloxy)-17β-hydroxy-7α,17α-dimethyl-4-androsten-19one acetate and 3β-(1'-cyclopentenyloxy)-17β-hydroxy-17α-vinyl-4-androsten-19-one acetate, respectively.

EXAMPLE 68

3β-TRIMETHYLSILOXY-4-ANDROSTENE-17β,19-DIOL 17-ACETATE

A solution of 4-androstene-3β,17β,19-triol 17,19-diacetate, trimethylchlorosilane and pyridine in toluene is refluxed for 24 hours. The solid is removed by filtration and the filtrate reduced to dryness and under vacuum. The oil is crystallized from hexane to yield 3β-trimethylsiloxy-4-androstene-17β,19-diol 17,19-diacetate. This produce is refluxed one hour with 1 equivalent of sodium bicarbonate in 10% aqueous methanol. The solution is poured onto water. The solid which forms is filtered, dried, and crystallized from ether-hexane to yield 3β-trimethylsiloxy-4-androstene-17β,19-diol 17-acetate.

Substituting 17α-methyl-4-methyl-4-androstene-3β,17β,19-triol 17,19-diacetate and 17α-ethinyl-4-androstene-3β,17β,19-triol 17,19-diacetate for the 4-androstene-3β,17β,19-triol 17,19-diacetate above results in the preparation of 17α-methyl-3β-trimethylsiloxy-4-androstene-17β,19-diol 17-acetate and 17α-ethinyl-3β-trimethylsiloxy-4-androstene-17β,19-diol 17-acetate.

EXAMPLE 69

17β-HYDROXY-3β-TRIMETHYLSILOXY-4-ANDROSTEN-19-ONE ACETATE

One equivalent of Jones Reagent is added to a solution of 3β-trimethylsiloxy-4-androstene-17β,19-diol 17-acetate in acetone at 5° C. After stirring for 15 minutes, the acetone layer is poured into cold water with vigorous stirring. The solid is filtered, washed with water and dried in a vacuum oven. Crystallization from hexane yields 17β-hydroxy-3β-trimethylsiloxy-4-androsten-19-one acetate.

Substituting 3β-trimethylsiloxy-17α-methyl-4-androstene-17β,19-diol 17-acetate and 17α-ethinyl-3β-trimethylsiloxy-4-androstene-17β,19-diol 17-acetate for the 3β-trimethylsiloxy-4-androstene-17β,19-diol 17-acetate above results in the formation of 17β-hydroxy-3β-trimethylsiloxy-17α-methyl-4-androsten-19-one acetate and 17α-ethinyl-17β-hydroxy-3β-trimethylsiloxy-4-androstene-19-one acetate.

EXAMPLE 70

3β,17β-DIHYDROXY-4-ANDROSTEN-19-ONE 17-ACETATE

A solution of 17β-hydroxy-3β-(2'-tetrahydropyranyloxy)-4-androsten-19-one acetate in a mixture of 60% acetic acid, 20% water, 20% tetrahydrofuran is permitted to stand overnight at room temperature. The mixture is poured onto water and the pH adjusted to 6-7 with a 20% sodium hydroxide solution. The solid is collected by vacuum filtration, washed with water and air dried. Crystallization from acetone-hexane yields 3β,17β-dihydroxy-4-androsten-19-one 17-acetate.

Substituting 17β-hydroxy-1α,7α-dimethyl-3β-(2-tetrahydropyranyloxy)-4-androsten-19-one acetate, 17β-hydroxy-6α,17α-dimethyl-3β-(2'-tetrahydropyranyloxy)-4-androsten-19-one acetate, 17β-hydroxy-4,17α-dimethyl-3β-(2'-tetrahydropyranyloxy)-4-androsten-19-one acetate and 17β-hydroxy-1α-methyl-3β-(2'-tetrahydropyranyloxy)-4-androsten-19-one acetate for the 17β-hydroxy-3β-(2'-tetrahydropyranyloxy)-4-androsten-19-one acetate above results in the formation of 3α,17β-dihydroxy-1α,7α-dimethyl-4-androsten-19-one 17β,17β-dihydroxy-6α,17α-dimethyl-4-androsten-19one 17-acetate, 3β,17β-dihydroxy-4,17α-dimethyl-4-androsten-19-one 17-acetate and 3β,17β-dihydroxy-1α-methyl-4-androsten-19-one 17-acetate, respectively.

EXAMPLE 71

ANDROST-4-ENE-3β,17β,19-TRIOL 19-ACETATE

A tetrahydrofuran solution of 19-hydroxy-4-androstene-3,17-dione acetate is added to lithium tri-t-butoxyaluminum hydride in tetrahydrofuran, and the resultant solution stirred overnight at room temperature. An aqueous solution of sodium potassium tartrate is added with stirring until a readily filterable precipitate forms. The filtrate is concentrated under reduced pressure and diluted with ether. The resulting solution is washed with water, dried over magnesium sulfate and the ether removed under vacuum. The residual androst-4-ene-3β, 17β,19-triol 19-acetate is crystallized from acetone.

EXAMPLE 72

3β,17β-DI-(2'-TETRAHYDROPYRANYLOXY)-4-ANDROSTEN-19-OL ACETATE

To a stirred solution of androst-4-ene-3β,17β,19-triol 19-acetate and p-toluenesulfonic acid in anhydrous dioxane at 20° C. is added dihydropyran dropwise. After standing for 5 minutes, methanolic ammonia is added until the solution is slightly basic. Removal of the solvent leaves an oil which is dissolved in methylenechloride. The methylenechloride solution is extracted with sodium hydrogen carbonate, dried over magnesium sulfate and concentrated under reduced pressure. Crystallization of the residual oil from pentane yields 3β,17β-di-(2'-tetrahydropyranyloxy)-4-androsten-19-ol acetate.

Substitution of androst-4-ene-3α,17β,19-triol 19-acetate for the androst-4-ene-3β,17β,19-triol 19-acetate above results in the preparation of 3α,17β-di-(2'-tetrahydropyranyloxy)-4-androsten-19-ol acetate.

EXAMPLE 73

3β,17β-DI-(2'-TETRAHYDROPYRANYLOXY)-4-ANDROSTEN-19-OL

A solution of 3β, 17β-di-(2'-tetrahydropyranyloxy)-4-androsten-19-ol acetate and one equivalent of sodium bicarbonate in 10% aqueous methanol are refluxed for one hour. The cooled solution is poured onto water and the oil which separates is extracted into ether. The ether layer is washed with water, dried over magnesium sulfate and concentrated. The residue which remains is crystallized from hexane to yield 3β,17β-di-(2'-tetrahydropyranyloxy)-4-androsten-19-ol.

Substituting 3β,17β-dimethoxy-4-androsten-19-ol acetate, 3β,17β-ditriphenylsiloxy-4-androsten-19-ol acetate and 3α,17β-di-(2'-tetrahydropyranyloxy)-4-androsten-19-ol acetate for the 3β,17β-di-(2'-tetrahydropyranyloxy)-4-androsten-19-ol acetate above results in the preparation of 3β,17β-dimethoxy-4-androsten-19-ol, 3β,17β-ditriphenylsiloxy-4-androsten-19-ol, and 3α-di-(2'-tetrahydropyranyloxy)-4-androsten-19-ol, respectively.

EXAMPLE 74

3β,17β-DI-(2'-TETRAHYDROPYRANYLOXY)-4-ANDROSTEN-19-ONE

One equivalent of Jones Reagent is added to an acetone solution of 3β,17β-di-(2'-tetrahydropyranyloxy)-4-androsten-19-ol at 0° C. After standing for 20 minutes the acetone layer is poured onto ice water with vigorous stirring. The solid is filtered, air dried and crystallized from hexane to yield the desired 3β,17β-di-(2'-tetrahydropyranyloxy)-4-androsten-19-one.

Substituting 3β,17β-dimethyloxy-4-androsten-19-ol, 3β,17β-ditriphenylsiloxy-4-androsten-19-ol and 3α,17β-di-(2'-tetrahydropyranyloxy)-4-androsten-19-ol for the 3β,17β-di-(2'-tetrahydropyranyloxy)-4-androsten-19-ol above result in the preparation of 3β,17β-dimethoxy-4-androsten-19-one, 3β,17β-ditriphenylsiloxy-4-androsten-19-one and 3α,17β-di-(2'-tetrahydropyranyloxy)-4-androsten-19-one, respectively.

EXAMPLE 75

3β,17β-DIHYDROXY-4-ANDROSTEN-19-ONE

A solution of 3β,17β-di-(2'-tetrahydropyranyloxy)-4-androsten-19-one in a mixture of 60% acetic acid, 20% water, 20% tetrahydrofuran is left at room temperature overnight. The mixture is poured onto water and the pH adjusted to 6–7 with a 20% sodium hydroxide solution. The solid is collected by vacuum filtration, washed with water and air dried. Crystallizaton from ether-hexane yields 3β,17β-dihydroxy-4-androsten-19-one.

EXAMPLE 76

3β,17β-DIMETHOXY-4-ANDROSTEN-19-OL ACETATE

Androst-4-ene-3β,17β,19-triol 19-triol 19-acetate is dissolved in methylenechloride and trimethyloxonium fluoroborate added. After stirring for 2 hours at room temperature, water is added. The methylenechloride layer is separated, dried over magnesium sulfate and concentrated. The residue which remains is crystallized from acetone-hexane to yield the desired 3β,17β-dimethoxy-4-androsten-19-ol acetate.

EXAMPLE 77

3β,16β-DITRIPHENYLSILOXY-4-ANDROSTEN-19-OL ACETATE

Androst-4-ene-3β,17β,19-triol 19-acetate, triphenylchlorosilane and pyridine are refluxed in toluene for a period of about 18 hours. The reaction mixture is filtered to remove pyridinium hydrochloride and the toluene is removed under vacuum. The residue which remains is crystallized from hexane to yield 3β,17β-ditriphenylsiloxy-4-androsten-19-ol acetate.

EXAMPLE 78

ANDROST-4-ENE-3α,17β,19-TRIOL 19-ACETATE

A 1 M solution of lithium tri-sec-butylborohydride in tetrahydrofuran under nitrogen is cooled in a dry ice-acetone bath to about −78° C. and 19-hydroxyandrost-4-ene-3,17-dione acetate in tetrahydrofuran is slowly added. The reaction mixture is stirred for a period of two hours at this temperature, warmed to 0° C., and stirring continued for an additional two hours. The reaction mixture is decomposed by the addition of 3 N sodium hydroxide followed by the addition of a 30% hydrogen peroxide solution. Care is taken that the solution temperature remains below 10° C. during decomposition. Solid potassium carbonate is added and the tetrahydrofuran decanted. The solid residue is washed with tetrahydrofuran and the combined solutions are dried over sodium sulfate, filtered and evaporated. The residue which remains is crystallized from acetone to yield 4-androstene-3α,17β,19-triol 19-acetate.

EXAMPLE 79

The following Example is illustrative of the behavioral activity for the compounds of this invention.

Copulatory behavioral tests are conducted in mature, sexually experienced Sprague-Dawley male rats that were either intact or castrated-adrenalectomized. Castration and adrenalectomy reduces the effect on behavior associated with endogenous steroids and/or their metabolites. The onset and intensity of behavioral responses related to mounting, intromission and ejaculation are determined both prior to and after an interval of at least two weeks post-surgery. Five animals per group are subcutaneously administered 500 micrograms/kg of 17β-hydroxy-androst-4-ene-3,19-dione propionate, testosterone or 0.25 ml/kg of olive oil vehicle for a period of 14 days. Ten minute behavioral observations are made in the presence of a receptive female rate on days 2, 8, 12 and 15 of the treatment period.

As shown in the table below at least two weeks after castration and adrenalectomy both the intromission frequency and the percent of animals responding is very low in comparison to their former intact state. Following testosterone treatment the castrated-adrenalectomized rats approach their pre-surgical sexual pattern of behavior after about 8 days of treatment. Castrated-adrenalectomized rats treated with 17β-hydroxy-androst-4-ene-3,19-dione propionate approach their pre-surgical sexual pattern of behavior after about day 12 of treatment. More importantly, the somatic androgenic effect upon the sex accessory organs of castrated-adrenalectomized rats receiving 17β-hydroxy-androst-4-ene-3,19-dione propionate is considerably less than with similar animals receiving testosterone.

| | Pre-Treatment | | | | Treatment Period (14 days) | | | | | | | |
|---|---|---|---|---|---|---|---|---|---|---|---|---|
| | Pre Surgery | | Post Surgery | | 2nd Day | | 8th Day | | 12th Day | | 15th Day | |
| Treatment | No. | % | No. | % | No. | % | No. | % | No. | % | No. | % |
| ADRENALECTOMIZED - CASTRATED | | | | | | | | | | | | |
| Vehicle (Olive Oil) | 15.6 | 100 | 2.4 | 20 | 3.4 | 20 | 0.0 | 0 | *NT | | 4.0 | 20 |
| Testosterone 500 μg/kg s.c. | 17.2 | 100 | 0.6 | 40 | 2.8 | 80 | 11.4 | 100 | *NT | | 19.8 | 100 |
| 17β-Hydroxy-androst-4-ene-3,19-dione propionate 500 μg/kg s.c. | 15.0 | 100 | 0.0 | 0 | *NT | | *NT | | 7.6 | 80 | *NT | |
| INTACT | | | | | | | | | | | | |
| Vehicle (Olive Oil) | 12.6 | 100 | 16.2 | 80 | 19.0 | 100 | 20.8 | 100 | *NT | | 19.6 | 100 |

*NT = Not Tested

EXAMPLE 80

PREPARATION OF A TABLET FORMULATION

One thousand tablets for oral use, each containing 25 mg of 17β-(1'-cyclohexenyloxy)-4-androstene-3,19-dione are prepared according to the following formulation:

| | Gm |
|---|---|
| (a) 17β-(1'-cyclohexenyloxy)-4-androstene-3,19-dione | 25 |
| (b) Dicalcium phosphate | 150 |
| (c) Methylcellulose, U.S.P. (15 cps) | 6.5 |
| (d) Talc | 20 |
| (d) Calcium stearate | 2.5 |

The 17β-(1'-cyclohexenyloxy)-4-androstene-3,19-dione and dicalcium phosphate are mixed well, granulated with a 7.5% aqueous solution of methylcellulose, passed through a No. 8 screen and carefully dried. The dried granules are passed through a No. 12 screen, blended with talc and calcium stearate and compressed into tablets.

EXAMPLE 81

PREPARATION OF A CAPSULE FORMULATION

One thousand two-piece hard gelatin capsules for oral use each containing 10 mg of 17β-(1'-cyclohexenyloxy)-3β-hydroxy-4-androstene-3,19-dione are prepared from the following ingredients:

| | Gm |
|---|---|
| (a) 17β-(1'-cyclohexenyloxy-3β-hydroxy-4-androstene-3,19-dione | 10 |
| (b) Lactose, U.S.P. | 100 |
| (c) Starch, U.S.P. | 10 |
| (d) Talc, U.S.P. | 5 |
| (e) Calcium stearate | 1 |

The finely powdered materials are mixed until uniformly dispersed and filled into hard shelled gelatin capsules of the apropriate size.

In a similar fashion one-piece soft gelatin capsules can be prepared in which the above formulation can be granulated, slugged or compressed directly into a rotary die or plate mold in which the capsule is formed. Alternatively, the above excipients may be omitted and the active ingredient dispensed as a powder directly into the capsule.

EXAMPLE 82

PREPARATION OF AN INTRAMUSCULAR INJECTION

A sterile aqueous suspension suitable for intramuscular injection is prepared from the following ingredients:

| | | Gm |
|---|---|---|
| (a) | 3β,17β-di-(2'-tetrahydropyranyloxy)-androst-4-en-19-one | 1 |
| (b) | Polyethylene glycol 4000, U.S.P. | 3 |
| (c) | Sodium chloride | 0.9 |
| (d) | Polyoxyethylene derivatives of sorbitan monooleate (TWEEN 80) U.S.P. | 0.4 |
| (e) | Sodium metabisulfite | 0.1 |
| (f) | Methylparaben, U.S.P. | 0.18 |
| (g) | Propylparaben, U.S.P. | 0.02 |
| (h) | Water for injection q.s. to 100 ml | |

The parabens, sodium metabisulfite and sodium chloride are dissolved in approximately one-half the volume of water for injection at 80° C. with stirring. The solution is cooled to below 40° C. and the active ingredient is dissolved therein followed by the polyethylene glycol 4,000 and polyoxyethylene derivatives of sorbitan monooleate. The cooled solution is adjusted to the final volume with water for injection and is then sterilized by sterile filtration through a suitable filter. Each one ml of solution contains 10 mg of 3β,17β-di-(2'-tetrahydropyranyloxy)-androst-4-en-19-one as the active ingredient.

We claim:
1. An androst-4-en-19-one having the formula:

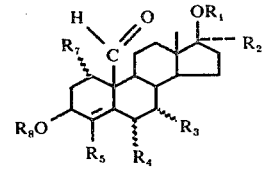

wherein
$R_1$ is selected from the group consisting of hydrogen, carboxylic acyl having from 1 to 12 carbon atoms, lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms;

$R_2$ is selected from the group consisting of hydrogen, lower alkyl having from 1 to 6 carbon atoms, lower alkenyl having from 2 to 6 carbon atoms, lower alkynyl having from 2 to 6 carbon atoms, and when $R_2$ and $OR_1$ are taken together is oxo;

$R_3$, $R_4$, $R_5$ and $R_7$ are hydrogen and methyl; and $R_8$ is lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalky group has from 5 to 7 carbon atoms.

2. An androst-4-en-19-one having the formula:

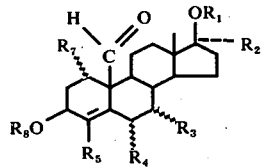

wherein $R_1$ and $R_8$ are selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms;

$R_2$ is selected from the group consisting of hydrogen, lower alkyl having from 1 to 6 carbon atoms, lower alkenyl having from 2 to 6 carbon atoms, lower alkynyl having from 2 to 6 carbon atoms, and when $R_2$ and $OR_1$ are taken together is oxo; and $R_3$, $R_4$, $R_5$ and $R_7$ are hydrogen and methyl.

* * * * *

UNITED STATES PATENT AND TRADEMARK OFFICE
CERTIFICATE OF CORRECTION

PATENT NO. : 4,022,769
DATED : May 10, 1977
INVENTOR(S) : Joyce F. Grunwell and Vladimir Petrow It is certified that error appears in the above-identified patent and that said Letters Patent are hereby corrected as shown below:

Column 1, line 33, "alkynyl" should read "alkenyl"; Column 3, line 27, "1-cyclopentyl" should read "1-cyclopentenyl"; Column 9, line 50, "androstandiene" should read "androstadiene"; Column 10, line 5, "androsten-31-" should read "androsten-3-"; Column 10, lines 31 and 33, "17β-" should read "17α-"; Column 10, line 45, "3β,19-diol" should read "3α,19-diol"; Column 10, line 50, "3β,17β,-" should read "3α,17β-"; Column 11, lines 14-15, "carbonate solution aqueous" should read "carbonate in aqueous"; Column 14, line 22, "-17β-" should read "-17α-"; Column 14, line 24, "-7β-" should read "-7α-"; Column 14, line 26, "6β,17β-" should read "6α,17α-"; Column 14, line 29, "17β-" should read "17α-"; Column 27, line 32, "lighium dimethylcopper is lithium" should read "lithium dimethylcopper is prepared"; Column 31, line 39, "19-hydroxy-1α-" should read "19-hydroxy-1α,7α-"; Column 31, line 44, "-1α,4-dimethyl-4-dimethyl-17β-" should read "-1α,4-dimethyl-17β-"; Column 32, line 46, "-4'-4-" should read "-4'-yloxy)-4-"; Column 33, line 39, prior to the word "and" a compound was omitted and should read "19-hydroxy-4,7α-dimethyl-17β-triphenylsiloxy-4-androst-3-one"; Column 34, line 1, "methyl-17α-" should read "methyl-17β-"; Column 34, line 22, "-3β,19-triol" should read "-3β,17β,19-triol"; Column 34, line 28, "-1β-methyl-" should read "-1α-methyl-"; Column 35, lines 3-4, "-3α,1-7α,19-triol" should read "-3β,17β,19-triol"; Column 35, line 51, "ANDROSTENE8-" should read "androstene-"; Column 36, line 14, "(1'-cyclopentyloxy)" should read "(1'-methoxy-1'-cyclopentyloxy)"; Column 37, line 33, "17α-methyl-4-methyl-4-androstene-" should read "17α-methyl-4-androstene-"; Column 38, line 17, "3α,17β-" should read "3β,17β-"; Column 38, line 18, "19-one 173β,17β-" should read "19-one 17-acetate, 3β,17β-";

UNITED STATES PATENT AND TRADEMARK OFFICE
CERTIFICATE OF CORRECTION

PATENT NO. : 4,022,769

DATED : May 10, 1977

INVENTOR(S) : Joyce F. Grunwell and Vladimir Petrow

It is certified that error appears in the above-identified patent and that said Letters Patent are hereby corrected as shown below:

Column 39, line 14, "3α-di-" should read "3α,17β-di-"; Column 39, line 54, "-3β,17β,19-triol 19-triol" should read "3β,17β,19-triol"; Column 39, line 65, "3β,16β-" should read "3β,17β-"; Column 43, line 21, "cycloaky" should read "cycloalkyl".

Signed and Sealed this

Twenty-eighth Day of March 1978

[SEAL]

Attest:

RUTH C. MASON
Attesting Officer

LUTRELLE F. PARKER
Acting Commissioner of Patents and Trademarks